(12) United States Patent
Barlaam et al.

(10) Patent No.: US 7,122,551 B2
(45) Date of Patent: Oct. 17, 2006

(54) METALLOPROTEINASE INHIBITOR COMPOUNDS

(75) Inventors: Bernard Christophe Barlaam, Reims (FR); Robert Ian Dowell, Cheshire (GB); Maurice Raymond Verschoyle Finlay, Cheshire (GB); Nicholas John Newcombe, Cheshire (GB); Howard Tucker, Cheshire (GB); David Waterson, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 100 days.

(21) Appl. No.: 10/787,813

(22) Filed: Feb. 26, 2004

(65) Prior Publication Data

US 2004/0176386 A1 Sep. 9, 2004

Related U.S. Application Data

(63) Continuation of application No. 09/788,687, filed on Feb. 21, 2001, now Pat. No. 6,734,183.

(30) Foreign Application Priority Data

Feb. 21, 2000 (GB) ................... 0400467.7

(51) Int. Cl.
C07D 403/12 (2006.01)
C07D 403/14 (2006.01)
A61K 31/4545 (2006.01)
A61P 9/10 (2006.01)

(52) U.S. Cl. .............. 514/255.05; 514/256; 514/316; 514/318; 544/295; 544/296; 544/333; 544/357; 546/192; 546/193; 546/194; 546/242; 546/247

(58) Field of Classification Search ............. 546/192, 546/193, 194, 242, 247; 544/295, 296, 333, 544/357; 514/255.05, 256, 316, 318
See application file for complete search history.

(56) References Cited

U.S. PATENT DOCUMENTS

| 5,998,412 A | 12/1999 | Broka et al. |
|---|---|---|
| 6,100,266 A | 8/2000 | Montana et al. |
| 6,130,220 A | 10/2000 | Broka et al. |
| 6,143,744 A | 11/2000 | Broka et al. |
| 6,235,786 B1 | 5/2001 | Dai et al. |
| 6,294,573 B1 | 9/2001 | Curtin et al. |
| 6,376,506 B1 | 4/2002 | Broka et al. |
| 6,479,502 B1 | 11/2002 | Martin |
| 6,482,827 B1 | 11/2002 | Alpegiani |
| 2003/0050310 A1 | 3/2003 | Martin |

FOREIGN PATENT DOCUMENTS

| DE | 19802350 | 7/1998 |
|---|---|---|
| WO | WO-98/16514 | 4/1998 |
| WO | WO-99/02510 | 1/1999 |
| WO | WO-99/38843 | 8/1999 |

*Primary Examiner*—Kahsay Habte
(74) *Attorney, Agent, or Firm*—Fish & Neave IP Group Ropes & Gray LLP

(57) ABSTRACT

Compounds of the formula I

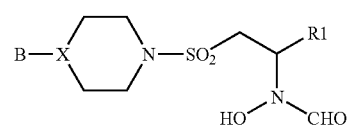

useful as metalloproteinase inhibitors, especially as inhibitors of MMP 13.

15 Claims, No Drawings

METALLOPROTEINASE INHIBITOR COMPOUNDS

RELATED APPLICATIONS

This application is a continuation of U.S. application Ser. No. 09/788,687, filed Feb. 21, 2001, now U.S. Pat. No. 6,734,183 which claims priority from United Kingdom Application No. 00400467.7, filed Feb. 21, 2000, the specifications of each of which are incorporated by reference herein.

The present invention relates to compounds useful in the inhibition of metalloproteinases and in particular to pharmaceutical compositions comprising these, as well as their use.

The compounds of this invention are inhibitors of one or more metalloproteinase enzymes. Metalloproteinases are a superfamily of proteinases (enzymes) whose numbers in recent years have increased dramatically. Based on structural and functional considerations these enzymes have been classified into families and subfamilies as described in N. M. Hooper (1994) FEBS Letters 354:1–6. Examples of metalloproteinases include the matrix metalloproteinases (MMP) such as the coliagenases (MMP1, MMP8, MMP13), the gelatinases (MMP2, MMP9), the stromelysins (MMP3, MMP10, MMP11), matrilysin (MMP7), metalloelastase (MMP12), enamelysin (MP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265–279).

Metalloproteinases have been associated with many disease conditions. Inhibition of the activity of one or more metalloproteinases may well be of benefit in these disease conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atherosclerosis; and chronic obstructive pulmonary diseases, COPD (for example, the role of MMPs such as MMP12 is discussed in Anderson & Shinagawa, 1999, Current Opinion in Anti-inflammatory and Immunomodulatory Investigational Drugs, 1(1): 29–38).

A number of metalloproteinase inhibitors are known; different classes of compounds may have different degrees of potency and selectivity for inhibiting various metalloproteinases. We have discovered a new class of compounds that are inhibitors of metalloproteinases and are of particular interest in inhibiting MMP-13, as well as MMP-9. The compounds of this invention have beneficial potency and/or pharmacokinetic properties.

MMP13, or collagenase 3, was initially cloned from a cDNA library derived from a breast tumour [J. M. P. Freije et al. (1994) Journal of Biological Chemistry 269(24): 16766–16773]. PCR-RNA analysis of RNAs from a wide range of tissues indicated that MMP13 expression was limited to breast carcinomas as it was not found in breast fibroadenomas, normal or resting mammary gland, placenta, liver, ovary, uterus, prostate or parotid gland or in breast cancer cell lines (T47-D, MCF-7 and ZR75-1). Subsequent to this observation MMP13 has been detected in transformed epidermal keratinocytes [N. Johansson et al., (1997) Cell Growth Differ. 8(2):243–250], squamous cell carcinomas [N. Johansson et al., (1997) Am. J. Pathol. 151(2):499–508] and epidermal tumours [K. Airola et al., (1997) J. Invest. Dermatol. 109(2):225–231]. These results are suggestive that MMP13 is secreted by transformed epithelial cells and may be involved in the extracellular matrix degradation and cell-matrix interaction associated with metastasis especially as observed in invasive breast cancer lesions and in malignant epithelia growth in skin carcinogenesis.

Recent published data implies that MMP13 plays a role in the turnover of other connective tissues. For instance, consistent with MMP13's substrate specificity and preference for degrading type II collagen [P. G. Mitchell et al., (1996) J. Clin. Invest. 97(3):761–768; V. Knauper et al., (1996) The Biochemical Journal 271:1544–1550], MMP13 has been hypothesised to serve a role during primary ossification and skeletal remodelling [M. Stahle-Backdahl et al., (1997) Lab. Invest. 76(5):717–728; N. Johansson et al., (1997) Dev. Dyn. 208(3):387–397], in destructive joint diseases such as rheumatoid and osteo-arthritis [D. Wernicke et al., (1996) J. Rheumatol. 23:590–595; P. G. Mitchell et al., (1996) J. Clin. Invest. 97(3):761–768; O. Lindy et al., (1997) Arthritis Rheum 40(8):1391–1399]; and during the aseptic loosening of hip replacements [S. Imai et al., (1998) J. Bone Joint Surg. Br. 80(4):701–710]. MMP13 has also been implicated in chronic adult periodontitis as it has been localised to the epithelium of chronically inflamed mucosa human gingival tissue [V. J. Uitto et al., (1998) Am. J. Pathol 152(6): 1489–1499] and in remodelling of the collagenous matrix in chronic wounds [M. Vaalamo et al., (1997) J. Invest. Dermatol. 109(1):96–101].

MMP9 (Gelatinase B; 92 kDa TypeIV Collagenase; 92 kDa Gelatinase) is a secreted protein which was first purified, then cloned and sequenced, in 1989 (S. M. Wilhelm et al (1989) J. Biol Chem. 264 (29): 17213–17221. Published erratum in J. Biol Chem. (1990) 265 (36): 22570). A recent review of MMP9 provides an excellent source for detailed information and references on this protease: T. H. Vu & Z. Werb (1998) (In: Matrix Metalloproteinases. 1998. Edited by W. C. Parks & R. P. Mecham. pp115–148. Academic Press. ISBN 0-12-545090-7). The following points are drawn from that review by T. H. Vu & Z. Werb (1998).

The expression of MMP9 is restricted normally to a few cell types, including trophoblasts, osteoclasts, neutrophils and macrophages. However, it's expression can be induced in these same cells and in other cell types by several mediators, including exposure of the cells to growth factors or cytokines. These are the same mediators often implicated in initiating an inflammatory response. As with other secreted MMPs, MMP9 is released as an inactive Pro-enzyme which is subsequently cleaved to form the enzymatically active enzyme. The proteases required for this activation in vivo are not known. The balance of active MMP9 versus inactive enzyme is further regulated in vivo by interaction with TIMP-1 (Tissue Inhibitor of Metalloproteinases-1), a naturally-occurring protein. TIMP-1 binds to the C-terminal region of MMP9, leading to inhibition of the catalytic domain of MMP9. The balance of induced expression of ProMMP9, cleavage of Pro- to active MMP9 and the presence of TIMP-1 combine to determine the amount of catalytically active MMP9 which is present at a local site. Proteolytically active MMP9 attacks substrates which include gelatin, elastin, and native Type IV and Type V collagens; it has no activity against native Type I collagen, proteoglycans or lamanins.

There has been a growing body of data implicating roles for MMP9 in various physiological and pathological processes. Physiological roles include the invasion of embryonic trophoblasts through the uterine epithelium in the early stages of embryonic implantation; some role in the growth and development of bones; and migration of inflammatory cells from the vasculature into tissues. Increased MMP9 expression has observed in certain pathological conditions, thereby implicating MMP9 in disease processed such as arthritis, tumour metastasis, Alzheimer's, Multiple Sclerosis, and plaque rupture in atherosclerosis leading to acute coronary conditions such as Myocardial Infarction.

WO-99/38843 claims compounds of the general formula

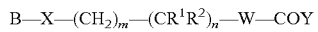

$$B—X—(CH_2)_m—(CR^1R^2)_n—W—COY$$

for use in the manufacture of a medicament for the treatment or prevention of a condition associated with matrix metalloproteinases. Specifically disclosed is the compound N-{1S-[4-(4-Chlorophenyl)piperazine-1-sulfonylmethyl]-2-methylpropyl}-N-hydroxyformamide.

We have now discovered compounds that are potent MMP13 inhibitors and have desirable activity profiles.

In a first aspect of the invention we now provide compounds of the formula I

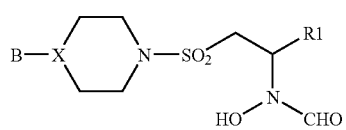

I wherein B represents a phenyl group monosubstituted at the 3- or 4-position by halogen or trifluoromethyl, or disubstituted at the 3- and 4-positions by halogen (which may be the same or different); or B represents a 2-pyridyl or 2-pyridyloxy group monosubstituted at the 4-, 5- or 6-position by halogen, trifluoromethyl, cyano or C1–4 alkyl; or B represents a 4-pyrimidinyl group optionally substituted at the 6-position by halogen or C1–4 alkyl;

X represents a carbon or nitrogen atom;
R1 represents a trimethyl-1-hydantoin C2–4alkyl or a trimethyl-3-hydantoin C2–4alkyl group; phenyl or C2–4alkylphenyl monosubstituted at the 3- or 4-position by halogen, trifluoromethyl, thio or C1–3alkyl or C1–3alkoxy; phenyl-SO2NHC2–4alkyl; 2-pyridyl or 2-pyridyl C2–4alkyl; 3-pyridyl or 3-pyridyl C2–4alkyl; 2-pyrimidine-SCH2CH2; 2- or 4-pyrimidinyl C2–4alkyl optionally monosubstituted by one of halogen, trifluoromethyl, C1–3alkyl, C1–3alkyloxy, 2-pyrazinyl optionally substituted by halogen or 2-pyrazinyl C2–4alkyl optionally substituted by halogen;

Any alkyl groups outlined above may be straight chain or branched.

Preferred compounds of the invention are those wherein any one or more of the following apply:

B represents 4-chlorophenyl, 4-fluorophenyl, 4-bromophenyl or 4-trifluorophenyl; 2-pyridyl or 2-pyridyloxy monosubstituted at the 4- or 5-position such as 5-chloro-2-pyridyl, 5-bromo-2-pyridyl, 5-fluoro-2-pyridyl, 5-trifluoromethyl-2-pyridyl, 5-cyano-2-pyridyl, 5-methyl-2-pyridyl; especially 4-fluorophenyl, 5-chloro-2-pyridyl or 5-trifluoromethyl-2-pyridyl;

X represents a nitrogen atom;

R1 is 3-chlorophenyl, 4-chlorophenyl, 3-pyridyl, 2-pyridylpropyl, 2- or 4-pyrimidinylethyl (optionally monosubstituted by fluorine), 2- or 4-pyrimidinylpropyl, 2-(2-pyrimidinyl)propyl (optionally monosubstitued by fluorine); especially 2-pyrimidinylpropyl, 2-(2-pyrimidinyl)propyl (optionally monosubstituted by fluorine) or 5-fluoro-2-pyrimidinylethyl.

For compounds of formula I, a particular subgroup is represented by compounds wherein B is a phenyl group monosubstituted at the 3- or 4-position by halogen or trifluoromethyl, or disubstituted at the 3- and 4-positions by halogen (which may be the same or different); or B is a 2-pyridyl or 2-pyridyloxy group monosubstituted at the 5- or 6-position by halogen, trifluoromethyl or cyano; or B is a 4-pyrimidinyl group optionally substituted at the 6-position by halogen or C1–4alkyl; X is a carbon or nitrogen atom; R1 is a trimethyl-1-hydantoin C2–4alkyl or a trimethyl-3-hydantoin C2–4alkyl group; or R1 is a phenyl or C2–4alkylphenyl monosubstituted at the 3- or 4-position by halogen, trifluoromethyl, thio or C1–3alkyl or C1–3alkoxy; or R1 is phenyl-SO2NHC2–4alkyl; or R1 is 2-pyridyl or 2-pyridyl C2–4alkyl; or R1 is 3-pyridyl or 3-pyridyl C2–4alkyl; or R1 is 2-pyrimidine-SCH2CH2; or R1 is 2- or 4-pyrimidinyl C2–4alkyl optionally monosubstituted by one of halogen, trifluoromethyl, C1–3alkyl, C 1–3 alkyloxy, 2-pyrazinyl or 2-pyrazinyl C2–4alky; any alkyl group may be straight chain or branched.

It will be appreciated that the particular substituents and number of substituents on B and/or R1 are selected so as to avoid sterically undesirable combinations.

Each exemplified compound represents a particular and independent aspect of the invention.

Where optically active centres exist in the compounds of formula I, we disclose all individual optically active forms and combinations of these as individual specific embodiments of the invention, as well as their corresponding racemates. Racemates may be separated into individual optically active forms using known procedures (cf. Advanced Organic Chemistry: 3rd Edition: author J March, p104–107) including for example the formation of diastereomeric derivatives having convenient optically active auxiliary species followed by separation and then cleavage of the auxiliary species.

It will be appreciated that the compounds according to the invention can contain one or more asymmetrically substituted carbon atoms. The presence of one or more of these asymmetric centres (chiral centres) in a compound of formula I can give rise to stereoisomers, and in each case the invention is to be understood to extend to all such stereoisomers, including enantiomers and diastereomers, and mixtures including racemic mixtures thereof.

In the examples we disclose the isolation and characterisation of certain enantiomers. Enantiomers may be prepared by the reaction of racemic material with a chiral auxilliary, separation of the diastereomers formed using chromatography, followed by subsequent cleavage of the chiral auxilliary. The diastereomer eluted second from the column (using conditions herein described) and subsequently cleaved gives the more active enantiomer when tested. In each case we believe the active enantiomer has S stereochemistry but do not wish to be limited by this initial determination. The active enantiomer is characterised by its derivative being eluted second from the separation column. Use of different compounds of formula I, alternative columns and/or different solvents may affect the elution order of the most active enantiomer.

In the examples we disclose the isolation and characterisation of certain diastereomers. Chromatographic separation and subsequent testing revealed that the more active diastereomer is eluted first from the separation column (ie the more active diastereomer is characterised by being eluted first from the separation column). Use of different compounds of formula I, alternative columns and/or different solvents may affect the elution order of the most active diastereomer.

For compounds of formula I with two chiral centres we believe the active enantiomer has S,S stereochemistry but do not wish to be limited by this initial determination.

Where tautomers exist in the compounds of formula I, we disclose all individual tautomeric forms and combinations of these as individual specific embodiments of the invention.

As previously outlined the compounds of the invention are metalloproteinase inhibitors, in particular they are inhibitors of MMP13. Each of the above indications for the compounds of the formula I represents an independent and particular embodiment of the invention. Whilst we do not wish to be bound by theoretical considerations, the compounds of the invention are believed to show selective inhibition for any one of the above indications relative to any MMP1 inhibitory activity, by way of non-limiting example they may show 100–1000 fold selectivity over any MMP1 inhibitory activity.

Certain compounds of the invention are of particular use as aggrecanase inhibitors ie. inhibitors of aggrecan degradation. Certain compounds of the invention are of particular use as inhibitors of MMP9 and/or MMP12.

The compounds of the invention may be provided as pharmaceutically acceptable salts. These include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

They may also be provided as in vivo hydrolysable esters. These are pharmaceutically acceptable esters that hydrolyse in the human body to produce the parent compound. Such esters can be identified by administering, for example intravenously to a test animal, the compound under test and subsequently examining the test animal's body fluids. Suitable in vivo hydrolysable esters for carboxy include methoxymethyl and for hydroxy include formyl and acetyl, especially acetyl.

In order to use a compound of the formula I or a pharmaceutically acceptable salt or in vivo hydrolysable ester thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula I or a pharmaceutically acceptable salt or an in vivo hydrolysable ester and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to hereinabove.

The pharmaceutical compositions of this invention will normally be administered to humans so that, for example, a daily dose of 0.5 to 75 mg/kg body weight (and preferably of 0.5 to 30 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention.

Therefore in a further aspect, the present invention provides a compound of the formula I or a pharmaceutically acceptable salt or in vivo hydrolysable ester thereof for use in a method of therapeutic treatment of the human or animal body. In particular we disclose use in the treatment of a disease or condition mediated by MMP13 and/or aggrecanase and/or MMP9 and/or MMP12.

In yet a further aspect the present invention provides a method of treating a metalloproteinase mediated disease condition which comprises administering to a warm-blooded animal a therapeutically effective amount of a compound of the formula I or a pharmaceutically acceptable salt or in vivo hydrolysable ester thereof. Metalloproteinase mediated disease conditions include arthritis (such as osteoarthritis), atherosclerosis, chronic obstructive pulmonary diseases (COPD).

In another aspect the present invention provides a process for preparing a compound of the formula I or a pharmaceutically acceptable salt or in vivo hydrolysable ester thereof which process comprises reacting a compound of the formula II with an appropriate compound of the formula R1CHO to yield an alkene of formula III, which is then converted to a compound of formula IV, which is a precursor to compound I, and optionally thereafter forming a pharmaceutically acceptable salt or in vivo hydrolysable ester of the compound of formula I, as set out below:

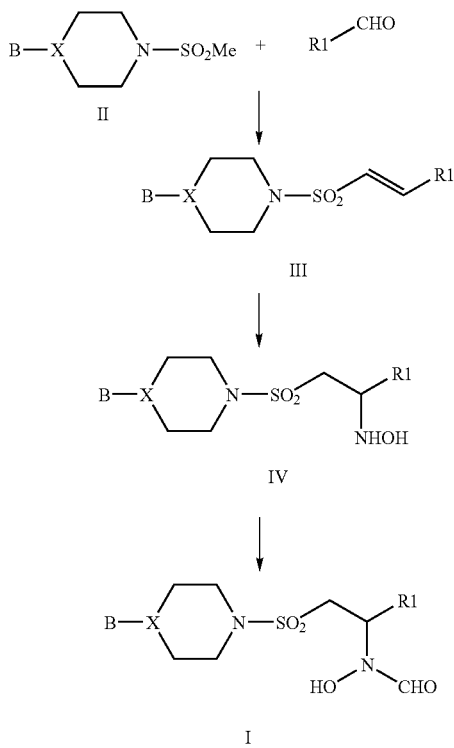

A compound of formula II is conveniently prepared by reacting a compound of formula V with a compound of formula VI, wherein B' is a precursor of B and X' represents X or a precursor of X or an activated form of X suitable for reaction with B'. II may also be prepared from compound VII as shown below:

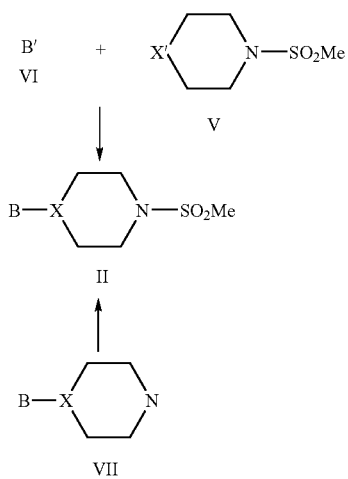

It will be appreciated that many of the relevant starting materials are commercially available. In addition the following table shows details of aldehyde intermediates and their corresponding registry numbers in Chemical Abstracts.

| RCHO | Chemical Abstracts Registry Numbers |
| --- | --- |
| 3-(2-pyrimidinylthio)-propionaldehyde | 155957-56-5 |
| 3-(2-pyrazinyl)butyraldehyde | 177615-94-0 |
| 3-phenylsulphonylamido-propanal | 57483-28-0 |
| 4-(4-methoxyphenyl)-butyraldehyde | 160093-24-3 |
| 4-(3-methoxyphenyl)-butyraldehyde | 113504-55-5 |

Aldehydes without Chemical Abstracts Registry Numbers 3-(2-pyrimidyl)propionaldehyde. To a solution of 2-Bromopyrimidine (7.95 g, 0.05 M) in acetonitrile (150 mL) was added propargylalcohol (4.2 g, 0.075 M), bis-(triphenylphosphine)-palladium(II)chloride (750 mg, 1 mM), copper iodide (100 mg, 0.5 mM) and triethylamine (25 mL, 0.25 M) and the mixture was stirred and heated at 70° C. for 2 hours. An additional amount of propargyl alcohol (2.1 g, 0.038 M), bis-(triphenylphosphine)-palladium(II)chloride (375 mg, 0.5 mil), and copper iodide (50 mg, 0.25 mil) was then added to the reaction mixture which was stirred and heated at 70° C. for an additional 1 hour.

The reaction mixture was evaporated to dryness and the residue which was pre-adsorbed on to silica, chromatographed. Elution with ethyl acetate gave 3-(2-pyrimidyl)prop-2-yn-3-ol as a yellow solid 4.45 g (66%). NMR (CDCl$_3$) 2.9 (1H, t), 4.5 (2H, d), 7.3 (1H, d), 8.8 (2H, t), MS found MH$^+$ 135.

3-(2-pyrimidyl)prop-2-yn-1-ol (4.45 g, 0.033 M) was dissolved in ethyl acetate (140 mL), 10% Pd/C (890 mg) was added and the mixture stirred under an atmosphere of hydrogen for 6 hours. The reaction mixture was filtered through Celite and the filtrate evaporated to give 3-(2-pyrimidyl)propan-1-ol as a yellow oil, 4.15 g (91%). NMR (CDCl$_3$) 2.1 (2H, m), 3.2 (2H, t), 3.8 (2H, t), 7.2 (1H, t), 8.7 (2H, d) MS found MH$^+$ 139.

3-(2-pyrimidyl)propan-1-ol was oxidized to give 3-(2-pyrimidyl)propionaldehyde using the following Swern conditions. To oxalyl chloride (14.3 ml) dissolved in dichloromethane (700 ml) was added DMSO (21.3 ml), maintaining the temperature below −60° C. After 15 minutes the alcohol (20.8 g) dissolved in dichloromethane (20 ml) was slowly added followed 30 minutes later by triethylamine (125 ml). After 15 minutes the reaction mixture was allowed to warm to room temperature when water (100 ml) was added. The solvents were separated and the organic layer was washed with water (3×150 ml), dried (MgSO$_4$) and evaporated to give an oil which was purified by flash column chromatography eluting with ethyl acetate/methanol (5%) to give the product (8.71 g, 43%) as an oil. NMR CDCl$_3$ 3.0 (2H, t), 3.4 (2H, t), 7.1 (1H, t), 8.7 (2H, d), 9.9 (1H, s).

Using the procedure described above the following aldehydes were prepared:

4-(2-pyrimidyl)butyraldehyde by using 3-butyn-1-ol in place of propargylalcohol NMR CDCl$_3$ 9.8(1H, s), 8.6 (2H, m), 7.15 (1H, m), 3.0 (2H, m), 2.5 (2H, m), 2.2 (2H, m).

3-(2-pyrazinyl)propionaldehyde by using 2-bromopyrazine in place of 2-bromopyrimidine NMR (d6-DMSO) 9.77 (s, 1H), 8.61 (d, 1H), 8.54 (dd, 1H), 8.46 (d, 1H), 3.10 (t, 2H), 2.92 (t, 2H).

4-(2-pyrazinyl)butyraldehyde by using 2-bromopyrazine in place of 2-bromopyrimidine and 3-butyn-1-ol in place of propargyl alcohol NMR (d6-DMSO) 9.68 (s, 1H), 8.56 (m, 2H), 8.49 (m, 1H), 2.80 (t, 2H), 2.5 (m, 2H), 1.96 (m, 2H).

4-(4-trifluoromethylpyrimidin-2-yl)butanal by using 2-chloro-4-trifluoropyrimidine [CAS registry number 33034-67-2] in place of 2-bromopyrimidine and 3-butyno-1-ol in place of propargyl alcohol $^1$H NMR (CDCl$_3$): 9.80 (s, 1 H), 8.92 (d, 1 H, J=5.0 Hz), 7.47 (d, 1 H, J=5.0 Hz) 3.11 (dd, 2 H, J 7.5, 7.5 Hz), 2.60 (dd, 2 H, J=6.1, 6.1 Hz), 2.21 (m, 3 H).

4-(5-fluoropyrimidin-2-yl)butanal by using 2-chloro-5-fluoro-pyrimidine [CAS registry number 62802-42-0] in place of 2-bromopyrimidine and 3-butyno-1-ol in place of propargyl alcohol $^1$H NMR (CDCl$_3$): 9.90 (s, 1 H), 8.52 (s, 2 H, J=5.0 Hz), 7.47, 3.47 is (m, 2 H), 3.33 (dd, 2 H, J=6.8, 6.8 Hz), 3.02 (m, 2 H).

4-(4-methoxypyrimidin-2-yl)butanal by using 2-chloro-4-methoxy-pyrimidine [CAS registry number 22536-63-6] in place of 2-bromopyrimidine and 3-butyno-1-ol in place of propargyl alcohol $^1$H NMR (CDCl$_3$): 9.80 (s, 1 H), 8.34 (d, 1 H, J=5.0 Hz), 6.55 (d, 1 H, J=5.0 Hz), 3.97 (s, 3 H), 2.91 (dd, 2 H, J=6.8, 6.8 Hz), 2.58 (m, 2 H), 2.20 (m, 2 H).

4-(5-ethylpyrimidin-2-yl)butanal by using 2-chloro-5-ethyl-pyrimidine [CAS registry number 111196-81-7] in place of 2-bromopyrimidine and 3-butyno-1-ol in place of propargyl alcohol $^1$H NMR (CDCl$_3$): 9.79 (s, 1 H), 8.51 (s, 2 H), 2.99 (dd, 2 H, J=7.4, 7.4 Hz), 2.54 (m, 4 H), 2.17 (p, 1 H, J=7.4 Hz), 1.04 (t, 2 H, J=7.2 Hz).

5-(2-pyrimidyl)pentanal by using 2-bromopyrimidine and 4-pentyn-1-ol in place of propargul alcohol: NMR (CDCl$_3$) 9.8 (1H, s), 8.65 (2H, m), 7.1 (1H, m), 3.0 (2H, m), 2.5 (2H, m), 1.9 (2H, m), 1.7 (2H, m).

3-(5-bromopyrimidin-2-yl)propanal by using 2-iodo-5-bromopyrimidine in place of 2-bromopyrimidine $^1$H NMR (CDCl$_3$): 9.90 (s, 1H), 8.70 (s, 2H), 3.30 (dd, 2H), 3.0 (dd, 2H).

4-(4-pyrimidyl)-butan-1-al. 2,4-Dicloropyrimidine (4.47 g, 0.03M) was dissolved in triethylamine (250 ml) under argon. (Ph$_3$P)$_2$PdCl$_2$ (420 mg, 0.006M, CuI (28 mg, 0.00015M) and 3-butyn-1-ol (2.36 ml, 0.03M) were added and the mixture was stirred at ambient temperature for 18 hrs. After evaporation to dryness, water (250 ml), was added and extracted with dichloromethane. The combined organic phases were dried and evaporated to dryness. The residual oil was chromatographed, eluting with iso-hexane/ethyl acetate 1:1 to yield 4-(2 chloro-4-pyrimidyl)-3-butyn-1-ol as an oil (3.3 g) NMR (CDCl$_3$) d, 8.5, (d, 1H); 7.3, (d, 1H); 3.9, (t, 2H); 2.8, (m, 2H); 1.6, (s, 1H). Mass Spec found MH+ 183. This material was hydrogenated as described above, but in the presence of 1 equivalent of triethylamine, to give the required saturated alcohol which was oxidised using the previously described Swern oxidation to give the required 4-(4-pyrimidyl)-butan-1-al. NMR CDCl$_3$ d, 9.8, (s, 1H); 9.1; (s, 1H); 8.5, (d, 1H); 7.1, (d, 1H); 2.8, (t, 2H); 2.5, (t, 2H); 2.1, (m, 2H). Mass spec found MH– 149.

3-(5-fluoropyrimidin-2-yl)propanal. To a stirred solution of (E)-1-ethoxy-3-(5-fluoropyrimidin-2-yl)prop-2-enyl ethyl ether and (Z)-1-ethoxy-3-(5-fluoropyrimidin-2-yl)prop-2-enyl ethyl ether (9.7 g, 43 mmol) in dry ethanol (100 ml) at room temperature under an atmosphere of argon, was added 10% palladium on activated charcoal (1.0 g). The reaction flask was then evacuated and filled with hydrogen gas. The mixture was then stirred for 18 hours at room temperature. The reaction was then filtered through a pad of celite and evaporated under reduced pressure to give a yellow oil (8.7 g, 89%). To a solution of this oil (15 g, 66 mmol) in THF (200 ml) at room temperature was added an aqueous solution of hydrochloric acid (36 ml of a 2M solution, 72 mmol) and the reaction was stirred at room temperature for 3 hours. The reaction was then diluted with ethyl acetate (100 ml) and the pH of the mixture brought to pH=9 by the addition of aqueous sodium hydrogen carbonate solution (saturated, 100 ml). The layers were then separated and the aqueous phase extracted with ethyl acetate (3×100 ml). The combined organic extracts were then dried (Na$_2$SO$_4$), filtered and evaporated under reduced pressure to give 3-(5-fluoro-pyrimidin-2-yl)propanal (16 g) which was used without further purification. $^1$H NMR (CDCl$_3$): 9.90 (s, 1 H), 8.50 (s, 2 H), 3.33 (dd, 2 H, J=6.9, 6.9 Hz), 3.00 (dd, 2 H, J=6.9, 6.9 Hz).

The starting material was obtained by the following method: To a solution of 2-chloro-5-fluoro-pyrimidine [CAS registry number 62802-42-0] (9.0 g, 68 mmol) and 1-tributylstannyl-3,3-diethoxyprop-1-ene (42.8 g, 102 mmol, 5:1 mixture of E:Z isomers) in dry DMF (140 ml) under an atmosphere of dry argon, was added sequentially solid potassium carbonate (9.4 g, 68 mmol), tetraethylammonium chloride (11.2 g, 68 mmol) and bis(triphenylphosphine)palladium(II)chloride (2.4 g, 3.4 mmol). The resulting mixture was then heated to 120° C. for 3 hours. The reaction was then cooled to room temperature and was diluted with water (100 ml) and diethyl ether (150 ml). This mixture was then filtered through a pad of celite. The layers were separated and the aqueous phase extracted with diethyl ether (3×100 ml). The combined organic extracts were then dried (MgSO$_4$), filtered and evaporated under reduced pressure. Flash chromatography (silica gel, 10% ethyl acetate in hexanes) then gave the product as a pale yellow oil and a 3:1 mixture of E:Z isomers (9.7 g, 63%).

E-isomer: $^1$H NMR (CDCl$_3$): 8.53 (s, 2 H), 6.99 (dd, 1 H, J=15.4, 4.1 Hz), 6.86 (d, 1 H, J=15.4 Hz), 5.14 (d, 1 H, J=4.1 Hz), 3.56 (m, 4 H), 1.24 (t, 6 H, J=7.1 Hz).

Z-isomer: $^1$H NMR (CDCl$_3$): 8.57 (s, 2 H), 6.65 (d, 1 H, J=12.1 Hz), 6.49 (d, 1 H, J=7.5 Hz), 6.09 (dd, 1 H, J=12.1, 7.5 Hz), 3.70 (m, 4 H), 1.21 (t, 6 H, J=7.1 Hz).

An analogous method was used to prepare the following aldehydes using the appropriately substituted 2-chloro-pyrimidine:

3-(4-methoxypyrimidin-2-yl)propanal $^1$H NMR (CDCl$_3$): 9.82 (s, 1 H), 8.34 (d, 1 H, J=8.4 Hz), 6.55 (d, 1 H, J=7,4 Hz), 3.91 (s, 3 H), 3.28 (dd, 2 H, J=7.4, 7.4 Hz) 2.99 (dd, 2 H, J=7.4, 7.4 Hz).

3-(4-trifluoromethylpyrimidin-2-yl)propanal $^1$H NMR (CDCl$_3$): 9.92 (s, 1 H), 8.90 (d, 1 H, J=5.0 Hz), 7.47 (d, 1 H, J=5.0 Hz), 3.43 (dd, 2 H, J=6.8, 6.8 Hz).3.07 (dd, 2 H, J=6.8, 6.8 Hz).

3-(5-ethylpyrimidin-2-yl)propanal $^1$H NMR (CDCl$_3$): 9.91 (s, 1 H), 8.49 (s, 2 H), 3.31 (dd, 2 H, J=6.9, 6.9 Hz) 2.98 (dd, 2 H, J=6.9, 6.9 Hz), 2.61 (q, 2 H, J=7.6 Hz), 1.26 (t, 3 H, J=7.6 Hz).

3,5,5-trimethyl-1-propanal hydantoin

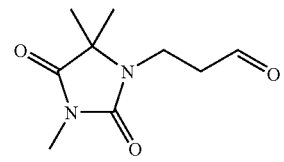

A solution of 3,5,5-trimethyl hydantoin [CAS (6345-19-3)] (3.5 g, 0.025 mol), 2-(2-bromoethyl)-1,3-dioxolane (4.8 ml, 0.041 mol), K₂CO₃ (8.5 g, 0.062 mol), benzyltrimethylammonium chloride (2.23 g, 0.012 mol) in MeCN (100 ml) was refluxed together for 24 hrs. Allowed the reaction to cool to RT and filtered, the filtrate was evaporated in vacuo. The residue was taken into DCM then washed with water (×3), before evaporating in vacuo. The residue was azeotroped with toluene (×3) to afford a yellow oil (5.4 g). The oil was then stirred in THF (30 ml) with conc. HCl (4 ml) at RT for 20 hrs. Neutralised with aqueous NaHCO3 and extracted with DCM (×8). The combined organics were dried over Na₂SO₄ and evaporated in vacuo to afford a yellow oil (4.3 g) ¹H NMR (CDCl₃): 9.82 (s, 1H), 3.62 (t, 2H), 3.04 (s, 3H), 2.90 (m, 2H), 1.37 (s, 6H).

1,5,5-trimethyl-3-propanal hydantoin

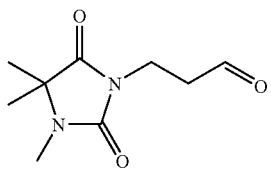

1,5,5-trimethylhydantoin [CAS (6851-81-6)] (5.0 g, 35.0 mol) was added to a mixture of NaOEt (0.02 g, 0.298 mmol, catalytic) and EtOH (8 ml), and stirred under Argon. The mixture was warmed to 30° C. before adding acrolein (2.35 ml) slowly, and the reaction exotherms to 45° C. The reaction was allowed to cool to RT and stirred for a further 2 hrs. AcOH (0.136 ml, 2.4 mmol) and silica gel (3.5 g) were added to the mixture before evaporating en vacuo. The product on silica was chromatagraphed on a silica column (eluant:5% acetone/DCM) to afford a clear oil (6.2 g). Further purification of the residue on alumina (eluant:DCM) afforded a clear oil (2.7 g). ¹H NMR (CDCl₃): 9.78 (s, 1H), 3.88 (t, 2H), 2.86 (s, 3H), 2.82 (m, 2H), 1.37 (s, 6H).

In an analogous manner 1,5,5-trimethyl-3-butanal hydantoin was prepared [M+H 213].

3-(3-chlorophenyl)butyraldehyde. A mixture of 3-chloroiodobenzene (2.38 g), palladium acetate (20 mg), sodium bicarbonate (1.01 g) and crotyl alcohol (1.28 ml) in N-methylpyrrolidone (4 ml) was stirred and heated at 130° C. for 2 hours. The reaction mixture was allowed to cool, water (50 ml) was added and the mixture was extracted with diethyl ether (2×50 ml). The combined organic extracts were dried and the residue obtained on removal of the solvent was purified by chromatography through silica eluting with a mixture of ethyl acetate and methylene chloride (1:20) to give the title compound as an oil, yield 519 mg, M−H=181

3-(2-pyridyl)butyraldehyde. Prepared by Swern oxidation of the corresponding alcohol (CAS 90642-86-7).

3-(5-fluoropyrimidin-2-yl)butanal

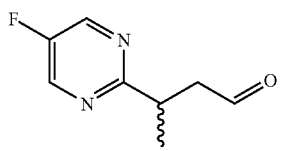

Concentrated hydrochloric acid (1 m) was added to a stirring solution of 2-[2-(1,3-dioxolan-2-yl)-1-methylethyl]-5-fluoropyrimidine (1.1 g) in tetrahydrofuran (10 ml) at ambient temperature, stirred for 3 hours then added solid sodium hydrogen carbonate to neutral pH. The mixture was poured onto a Chemelute carrtridge and washed with ethyl acetate (3×20 ml), the combined organics were dried over Na₂SO₄ and evaporated in vacuo to afford 3-(5-fluoropyrimidin-2-yl)butanal (300 mg, 35%) which was used without further purification.

The starting material was prepared as follows:

2-[2-(1,3-dioxolan-2-yl)-1-methylethyl]-5-fluoropyrimidine

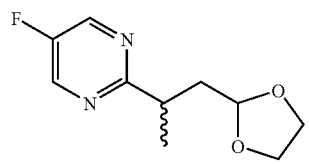

To a stirring suspension of activated "Rieke" zinc in tetrahydrofuran (21 ml, 1.53M) was added 2-(2-bromopropyl)-1,3-dioxolane (6.6 g) in tetrahydrofuran (50 ml), a rise in temperature from 21° C. to 40° C. was observed, heated at 40° C. for 1 hour then allowed to cool to ambient temperature before adding 2-chloro-5-fluoropyrimidine (3 g) and [1,2-Bis(diphenylphosphino)-propane]dichloronickel (II)chloride (368 mg). The mixture was stirred at ambient temperature for 4 hours then filtered through a pad of celite and the filtrate evaporated under reduced pressure. Flash chromatography (silica gel, haxane-25% ethyl acetate in hexanes) then gave the product as a pale yellow oil (1.1 g); ¹H NMR (d6-DMSO): 8.81 (s, 2H), 4.73 (dd, 1H), 3.66–3.87 (m, 4H), 3.21–3.30 (m, 1H), 2.19 (ddd, 1H), 1.83 (ddd, 1H), 1.27(d, 3H); m/z 213 (M+1).

2-(2-bromopropyl)-1,3-dioxolane

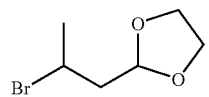

Crotonaldehyde (9.18 g, 108 mmol) was added dropwise to a stirring solution of bromotrimethylsilane (24 g, 156 mmol) at 0° C., stirred for 1 hour at 0° C. then warmed to room temperature and stirred for a further 1 hour. Ethylene glycol (9.5 g, 156 mmol) and p-tolunesulphonic acid (100 mg) was added and the solution was heated to reflux, water was removed by use of Dean and Stark apparatus. On completion the mixture was cooled to room temperature and washed with aqueous sodiumhydrogen carbonate solution (saturated, 2×50 ml).The residue was purified by vacuum distillation to give 2-(2-bromopropyl)-1,3-dioxolane (18.8 g, 40–42° C. @1 mm Hg, 89%)

¹H NMR (CDCl₃): 5.05 (dd, 1H), 4.18–4.33 (m, 1H), 3.84–4.0 (m, 4H), 2.25 (ddd, 1H), 2.03 (ddd, 1H), 1.75 (d, 3H).

An analogous method was used to prepare the following aldehydes using the appropriately substituted 2-chloro-pyrimidine and 1,3-dioxolane:

3-(5-chloropyrimidin-2-yl)propanal

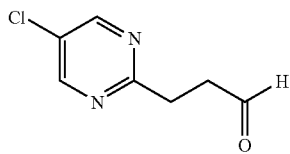

$^1$H NMR (CDCl$_3$): 9.90 (s, 1H), 8.60 (s, 2H), 3.32 (dd, 2H), 3.04 (dd, 2H).

3-(5-chloropyrimidin-2-yl)butanal

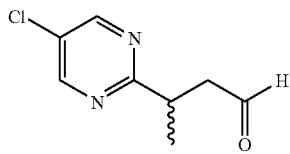

$^1$H NMR (CDCl$_3$): 9.85 (s, 1H), 8.60 (s, 2H), 3.65 (m, 1H), 3.14 (dd, 1H), 2.75 (dd, 1H), 1.39 (d, 3H).

3-[2-(6-Chloropyrazinyl)]propanal

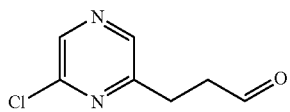

3-[2-(6-Chloropyrazinyl)]propanal diethyl acetal (200 mg, 0.82 mmol) was treated with 2N hydrochloric acid (450 µl) in tetrahydrofuran (2.5 ml) at room temperature for 18 h. After adjusting the pH to 8 using saturated aqueous sodium bicarbonate, the reaction was extracted (×3) with ethyl acetate and the organics dried (anyhdrous sodium sulfate), filtered and concentrated in vacuo to give the title compound as a dark brown oil (137 mg, 98%). This material was used without further purification.

$^1$H NMR (CDCl$_3$) δ 9.85 (1H, s); 8.4 (2H, 2×s); 3.5 (2H, t); 3.0 (2H, t).

The starting material was obtained by the following method:

3-[2-(6-Chloropyrazinyl)]propanal diethyl acetal

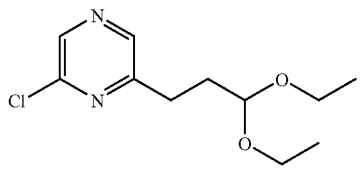

3-[2-(6-Chloropyrazinyl)]propynal diethyl acetal, (5.5 g, 22.9 mmol) in ethanol (55 ml) was degassed with argon and platinum (IV) oxide (52 mg, 0.23 mmol) added. The reaction vessel was evacuated and an atmosphere of hydrogen was introduced. After 2 days the reaction mixture was concentrated in vacuo and purified by flash chromatography, eluting with a gradient of 0–50% ethyl acetate in iso-hexane, to give 3-[2-(6-Chloropyrazinyl)]propanal diethyl acetal as a pale yellow oil (1.17 g, 21%).

$^1$H NMR (CDCl$_3$) δ 8.4 (1H, s); 8.35 (1H, s); 4.5 (1H, t); 3.75–3.55 (2H, m); 3.55–3.4 (2H, m); 2.9 (2H, dd); 2.1 (2H, dd); 1.2 (6H, t).

3-[2-(6-Chloropyrazinyl)]propynal diethyl acetal

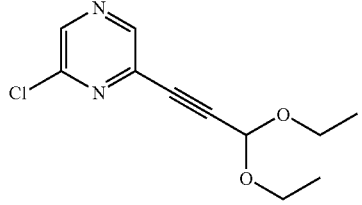

To a solution of 2,6-dichloropyrazine (1 g, 6.7 mmol) and propionaldehyde diethyl acetal (1.1 ml, 7.4 mmol) in acetonitrile (10 ml) at room temperature under an atmosphere of argon was added bis(triphenylphosphine)palladium(II) dichloride (94 mg, 0.13 mmol) and copper (I) iodide (51 mg, 0.27 mmol), followed by triethylamine (4.7 ml, 33.6 mmol). The reaction was stirred at room temperature over night. The solvent was removed in vacuo and the residue purified by flash chromatography, eluting with 10–20% ethyl acetate in iso-hexane, to give 3-[2-(6-Chloropyrazinyl)]propynal diethyl acetal as a yellow oil (660 mg, 41%).

$^1$H NMR (CDCl$_3$) δ 8.6 (1H, s); 8.55 (1H, s); 5.5 (1H, s); 3.9–3.75 (2H, m); 3.7–3.4 (2H, m); 1.25 (6H, t). m/s (EI$^+$) 241/243 (MH$^+$).

An alternative process for preparing a compound of the formula I or a pharmaceutically acceptable salt or in vivo hydrolysable ester thereof comprises reacting a compound of the formula II with a compound of the formula R1COOR to yield a compound of the formula VIII, converting this to a compound of the formula IX, converting the compound of formula IX to an alkene of formula III, which is then converted to a compound of formula IV, which is a precursor to compound I, and optionally thereafter forming a pharmaceutically acceptable salt or in vivo hydrolysable ester of the compound of formula I, as set out below:

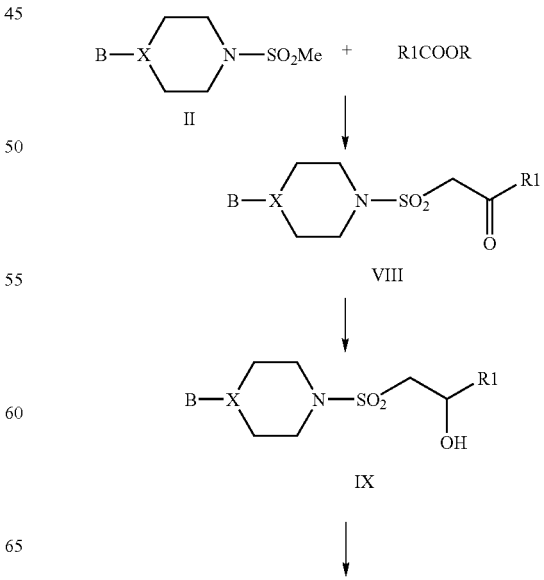

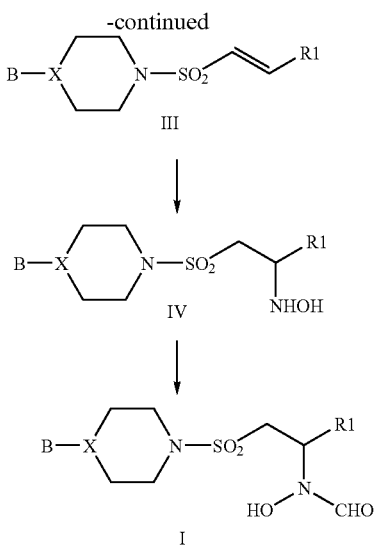

Appropriate esters of the formula R1COOR may be commercially or otherwise available or may be produced using, for example, an analogous procedure to that described in Example 10. It will be appreciated that it is possible to use any ester of the formula R1COOR (wherein R1 is as previously defined):—R may be any group including, for example, alkyl, aralkyl, heteroaryl etc.

The compounds of the invention may be evaluated for example in the following assays:

Isolated Enzyme Assays

Matrix Metalloproteinase Family Including for Example MMP13

Recombinant human proMMP13 may be expressed and purified as described by Knauper et al. [V. Knauper et al., (1996) The Biochemical Journal 271:1544–1550 (1996)].

The purified enzyme can be used to monitor inhibitors of activity as follows: purified proMMP13 is activated using 1 mM amino phenyl mercuric acid (APMA), 20 hours at 21° C.; the activated MMP13 (11.25 ng per assay) is incubated for 4–5 hours at 35° C. in assay buffer (0.1M Tris-HCl, pH 7.5 containing 0.1M NaCl, 20 mM CaCl2, 0.02 mM ZnCl and 0.05% (w/v) Brij 35 using the synthetic substrate 7-methoxycoumarin-4-yl)acetyl.Pro.Leu.Gly.Leu.N-3-(2,4-dinitrophenyl)-L-2,3-diaminopropionyl.Ala.Arg.NH$_2$ in the presence or absence of inhibitors. Activity is determined by measuring the fluorescence at λex 328 nm and λem 393 nm. Percent inhibition is calculated as follows: % Inhibition is equal to the [Fluorescence$_{plus\ inhibitor}$–Fluorescence$_{background}$] divided by the [Fluorescence$_{minus\ inhibitor}$–Fluorescence$_{background}$].

A similar protocol can be used for other expressed and purified pro MMPs using substrates and buffers conditions optimal for the particular MMP, for instance as described in C. Graham Knight et al., (1992) FEBS Lett. 296(3):263–266.

Adamalysin Family Including for Example TNF Convertase

The ability of the compounds to inhibit proTNFα convertase enzyme may be assessed using a partially purified, isolated enzyme assay, the enzyme being obtained from the membranes of THP-1 as described by K. M. Mohler et al., (1994) Nature 370:218–220. The purified enzyme activity and inhibition thereof is determined by incubating the partially purified enzyme in the presence or absence of test compounds using the substrate 4',5'-Dimethoxy-fluoresceinyl Ser.Pro.Leu.Ala.Gln.Ala.Val.Arg.Ser.Ser.Ser.Arg.Cys (4-(3-succinimid-1-yl)-fluorescein)-NH$_2$ in assay buffer (50 mM Tris HCl, pH 7.4 containing 0.1% (w/v) Triton X-100 and 2 mM CaCl$_2$), at 26° C. for 18 hours. The amount of inhibition is determined as for MMP13 except λex 490 nm and λem 530 nm were used. The substrate was synthesised as follows. The peptidic part of the substrate was assembled on Fmoc-NH-Rink-MBHA-polystyrene resin either manually or on an automated peptide synthesiser by standard methods involving the use of Fmoc-amino acids and O-benzotriazol-1-yl-N,N,N',N'-tetramnethyluronium hexafluorophosphate (HBTU) as coupling agent with at least a 4- or 5-fold excess of Fmoc-amino acid and HBTU. Ser[1] and Pro[2] were double-coupled. The following side chain protection strategy was employed; Ser[1](But), Gln[5](Trityl), Arg[8,12] (Pmc or Pbf), Ser[9,10,11](Trityl), Cys[13](Trityl). Following assembly, the N-terminal Fmoc-protecting group was removed by treating the Fmoc-peptidyl-resin with in DMF. The amino-peptidyl-resin so obtained was acylated by treatment for 1.5–2 hr at 70° C. with 1.5–2 equivalents of 4',5'-dimethoxy-fluorescein-4(5)-carboxylic acid [Khanna & Ullman, (1980) Anal Biochem. 108:156–161) which had been preactivated with diisopropylcarbodiimide and 1-hydroxybenzotriazole in DMF]. The dimethoxyfluoresceinyl-peptide was then simultaneously deprotected and cleaved from the resin by treatment with trifluoroacetic acid containing 5% each of water and triethylsilane. The dimethoxyfluoresceinyl-peptide was isolated by evaporation, trituration with diethyl ether and filtration. The isolated peptide was reacted with 4-(N-maleimido)-fluorescein in DMF containing diisopropylethylamine, the product purified by RP-HPLC and finally isolated by freeze-drying from aqueous acetic acid. The product was characterised by MALDI-TOF MS and amino acid analysis.

Natural Substrates

The activity of the compounds of the invention as inhibitors of aggrecan degradation may be assayed using methods for example based on the disclosures of E. C. Arner et al., (1998) Osteoarthritis and Cartilage 6:214–228; (1999) Journal of Biological Chemistry, 274 (10), 6594–6601 and the antibodies described therein. The potency of compounds to act as inhibitors against collagenases can be determined as described by T. Cawston and A. Barrett (1979) Anal. Biochem. 99:340–345.

Inhibition of Mettalloproteinase Activity in Cell/Tissue Based Activity

Test as an Agent to Inhibit Membrane Sheddases such as TNF Convertase

The ability of the compounds of this invention to inhibit the cellular processing of TNFα production may be assessed in THP-1 cells using an ELISA to detect released TNF essentially as described K. M. Mohler et al., (1994) Nature 370:218–220. In a similar fashion the processing or shedding of other membrane molecules such as those described in N. M. Hooper et al., (1997) Biochem. J. 321:265–279 may be tested using appropriate cell lines and with suitable antibodies to detect the shed protein.

Test as an Agent to Inhibit Cell Based Invasion

The ability of the compound of this invention to inhibit the migration of cells in an invasion assay may be determined as described in A. Albini et al., (1987) Cancer Research 47:3239–3245.

Test as an Agent to Inhibit Whole Blood TNF Sheddase Activity

The ability of the compounds of this invention to inhibit TNFα production is assessed in a human whole blood assay where LPS is used to stimulate the release of TNFα. Heparinized (10 Units/ml) human blood obtained from volunteers is diluted 1:5 with medium (RPMI1640+bicarbonate, penicillin, streptomycin and glutamine) and incubated (160 µl) with 20 µl of test compound (triplicates), in DMSO or appropriate vehicle, for 30 min at 37° C. in a humidified (5% $CO_2$/95% air) incubator, prior to addition of 20 µl LPS (E. coli. 0111:B4; final concentration 10 µg/ml). Each assay includes controls of diluted blood incubated with medium alone (6 wells/plate) or a known TNFα inhibitor as standard. The plates are then incubated for 6 hours at 37° C. (humidified incubator), centrifuged (2000 rpm for 10 min; 4° C.), plasma harvested (50–100 µl) and stored in 96 well plates at −70° C. before subsequent analysis for TNFα concentration by ELISA.

Test as an Agent to Inhibit in vitro Cartilage Degradation

The ability of the compounds of this invention to inhibit the degradation of the aggrecan or colfagen components of cartilage can be assessed essentially as described by K. M. Bottomley et al., (1997) Biochem J. 323:483–488.

Pharmacodynamic Test

To evaluate the clearance properties and bioavailability of the compounds of this invention an ex vivo pharmacodynamic test is employed which utilises the synthetic substrate assays above or alternatively HPLC or Mass spectrometric analysis. This is a generic test which can be used to estimate the clearance rate of compounds across a range of species. Animals (e.g. rats, marmosets) are dosed iv or po with a soluble formulation of compound (such as 20% w/v DMSO, 60% w/v PEG400) and at subsequent time points (e.g. 5, 15, 30, 60, 120, 240, 480, 720, 1220 mins) the blood samples are taken from an appropriate vessel into 10 U heparin. Plasma fractions are obtained following centrifugation and the plasma proteins precipitated with acetonitrile (80% w/v final concentration). After 30 mins at −20° C. the plasma proteins are sedimented by centrifugation and the supernatant fraction is evaporated to dryness using a Savant speed vac. The sediment is reconstituted in assay buffer and subsequently analysed for compound content using the synthetic substrate assay. Briefly, a compound concentration-response curve is constructed for the compound undergoing evaluation. Serial dilutions of the reconstituted plasma extracts are assessed for activity and the amount of compound present in the original plasma sample is calculated using the concentration-response curve taking into account the total plasma dilution factor.

In Vivo Assessment

Test as an Anti-TNF Agent

The ability of the compounds of this invention as ex vivo TNFα inhibitors is assessed in the rat. Briefly, groups of male Wistar Alderley Park (AP) rats (180–210 g) are dosed with compound (6 rats) or drug vehicle (10 rats) by the appropriate route e.g. peroral (p.o.), intraperitoneal (i.p.), subcutaneous (s.c.). Ninety minutes later rats are sacrificed using a rising concentration of $CO_2$ and bled out via the posterior vena cavae into 5 Units of sodium heparin/ml blood. Blood samples are immediately placed on ice and centrifuged at 2000 rpm for 10 min at 4° C. and the harvested plasmas frozen at −20° C. for subsequent assay of their effect on TNFα production by LPS-stimulated human blood. The rat plasma samples are thawed and 175 µl of each sample are added to a set format pattern in a 96 U well plate. Fifty µl of heparinized human blood is then added to each well, mixed and the plate is incubated for 30 min at 37° C. (humidified incubator). LPS (25 µl; final concentration 10 µg/ml) is added to the wells and incubation continued for a further 5.5 hours. Control wells are incubated with 25 µl of medium alone. Plates are then centrifuged for 10 min at 2000 rpm and 200 µl of the supernatants are transferred to a 96 well plate and frozen at −20° C. for subsequent analysis of TNF concentration by ELISA.

Data analysis by dedicated software calculates for each compound/dose:

Percent inhibition of TNFα=Mean TNFα (Controls)−Mean TNFα (Treated)×100 Mean TNFα (Controls)

Test as an Anti-Arthritic Agent

Activity of a compound as an anti-arthritic is tested in the collagen-induced arthritis (CIA) as defined by D. E. Trentham et al., (1977) J. Exp. Med. 146,:857. In this model acid soluble native type II collagen causes polyarthritis in rats when administered in Freunds incomplete adjuvant. Similar conditions can be used to induce arthritis in mice and primates.

Test as an Anti-Cancer Agent

Activity of a compound as an anti-cancer agent may be assessed essentially as described in I. J. Fidler (1978) Methods in Cancer Research 15:399–439, using for example the B16 cell line (described in B. Hibner et al., Abstract 283 p75 10th NCI-EORTC Symposium, Amsterdam Jun. 16–19, 1998).

The invention will now be illustrated but not limited by the following Examples:

EXAMPLE 1

N-[1-([4-(4-bromophenyl)piperazino]sulfonylmethyl)-4-pyrimidin-2-ylbutyl]-N-hydroxyformamide

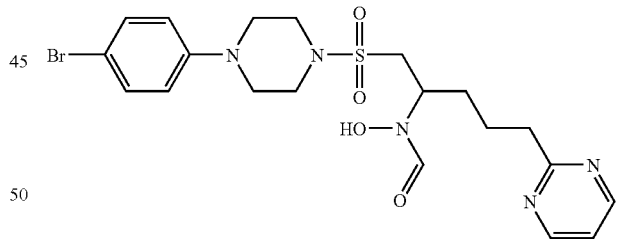

To a stirred solution of N-[1-([4-(4-bromophenyl)piperazino]sulfonylmethyl)-4-pyrimidin-2-ylbutyl]hydroxylamine (497 mg, 1.0 mmol) in THF (5.0 ml) and formic acid (2.5 ml), cooled to 0° C., was added a preformed mixture of acetic anhydride (566 µl, 6.0 mmol) and formic acid (2.0 ml). The mixture was stirred at 0° C. for 1 hour and allowed to come to room temperature. The solvents were removed by rotary evaporation and the residue purified by chromatography (50 g Silica Bond Elute, eluent 0→15% Methanol/Dichloromethane), pure fractions evaporated, and crystallised from hot ethyl acetate to give N-[1-([4-(4-bromophenyl)piperazino]sulfonylmethyl)-4-pyrimidin-2-ylbutyl]-N-hydroxyformamide as a white crystalline powder (262 mg, 51%).

NMR (300 MHz DMSO-$d_6$) δ/ppm: 9.87 (s, 1H*), 9.55 (s, 1H*), 8.70 (m, 2H), 8.29 (s, 1H*), 7.98 (s, 1H*), 7.33 (m, 3H), 6.92 (dd, 2H), 4.68 (m, 1H*), 4.13 (m, 1H*), 3.55–3.31 (m, 5H, partially obscured), 3.25–3.09 (m, 7H, partially obscured), 1.80–1.50 (m, 4H). MS: ES$^+$, (M+H)$^+$=512, 514 (Br Isotope Pattern).

* rotameric signals

The starting material was prepared as follows:

i) To a solution of 1-(4-bromophenyl)piperazine hydrochloride (5.09 g, 18.3 mmol) and triethylamine (7.67 ml) in dichloromethane (100 ml) was added methanesulfonyl chloride (2.83 ml, 36.3 mmol) dropwise. The mixture was stirred for 1 hour at room temperature then dichloromethane (100 ml) was added. The organics were washed with water (2×), brine and dried ($Na_2SO_4$) and evaporated in vacuo to a yellow solid which crystallised from Ethanol and washed with diethyl ether to give 1-(4-bromophenyl)-4-(methanesulfonyl)piperazine (4.74 g, 81% yield) as a white fluffy powder.

$^1$H NMR (300 MHz $CDCl_3$) δ/ppm: 7.38 (d, 2H), 6.91 (d, 2H), 3.21 (m, 8H), 2.89 (s, 3H). MS: ES+, (M+H)$^+$=318, 320 (Br isotope pattern).

ii) To the 1-(4-bromophenyl)-4-(methanesulfonyl)piperazine (902 mg, 2.0 mmol) suspended in anhydrous THF (15 ml), under Nitrogen, cooled to between −20 and −30° C. was added sequentially Lithium bis(trimethylsilyl)amide (1.0M in THF, 4.0 ml), Chlorotrimethylsilane (217 mg, 2.0 mmol, 253 μl) and 4-pyrimidin-2-ylbutanal (300 mg, 2.0 mmol). The mixture was stirred at −20° C. for 1 hour, quenched with saturated ammonium chloride solution and allowed to stand at ambient temperature overnight. The solvents were removed in vacuo and the residue partitioned between dichloromethane (15 ml) and water (5 ml), the organics separated and chromatogrammed (50 g Silica Bond Elute, eluted with 0→100% Ethyl Acetate/Hexane gradient) to give the 2-(5-[4-(4-bromophenyl)piperazino]sulfonylpent-4-enyl)pyrimidine as a white crystalline material (759 mg, 84% Yield)

MS: ES$^+$, (M+H)$^+$=451, 453 (Br isotope pattern).

iii) To a stirred solution of the 2-((E)-5-[4-(4-bromophenyl)piperazino]sulfonylpent-4-enyl)pyrimidine (451 mg, 1.0 mmol) in THF (10 ml) was added Hydroxylamine (50% solution in water, 500 μl) and the mixture stirred overnight. The solvents were removed in vacuo, azeotroping with toluene (3×) to give the N-[1-([4-(4-bromophenyl)piperazino]sulfonylmethyl)-4-pyrimidin-2-ylbutyl]hydroxylamine (497 mg, quantitative)

MS: ES$^+$, (M+H)$^+$=484, 486 (Br isotope pattern).

EXAMPLE 2

N-[1-([4-(5-chloropyridin-2-yl)piperazino]sulfonylmethyl)-3-(5-fluoropyrimidin-2-yl)propyl]-N-hydroxyformamide

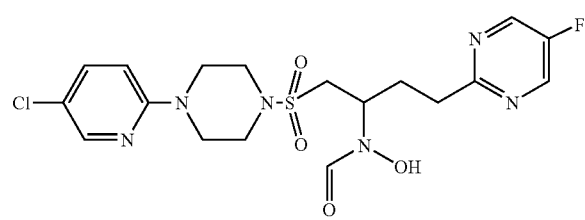

Acetic anhydride (0.51 ml) was added directly to formic acid (2.0 ml) which had been cooled to 0° C. and then added a solution of 2-[4-[4-(5-chloropyridin-2-yl)piperazino]sulfonyl-3-(hydroxyamino)butyl]-5-fluoropyrimidine (0.485 g) in tetrahydrofuran (11 ml). The solution was stirred at room temperature for 3 hours and then evaporated in vacuo, the resulting residue was azeotroped with toluene and then it was dissolved in methanol and heated to 40° C. for 30 minutes. The solution was evaporated to dryness and then added diethylether and stirred at room temperature for 10 minutes, solid filtered, dried in vacuo to give N-[1-([4-(5-chloropyridin-2-yl)piperazino]sulfonylmethyl)-3-(5-fluoropyrimidin-2-yl)propyl]-N-hydroxyformamide, (0218 g), mp 154–155° C.

NMR (d6-DMSO 373° K): 2.20 (m, 2H), 2.95 (m, 2H), 3.23 (dd, 1H), 3.30 (m, 4H), 3.49 (dd, 1H), 3.60 (m, 4H), 4.42 (vbs, 1H), 6.88 (d, 1H), 7.59 (dd, 1H), 8.05 (vbs, 1H), 8.12 (dd, 1H), 8.71 (s, 2H), 9.40 (vbs, 1H); m/z 473 (M+1).

The starting material was prepared as follows:

(i) 1-(5-chloropyridin-2-yl)-4-(methylsulfonyl)piperazine (0.600 g) was stirred in anhydrous tetrahydrofuran (22 ml) under Argon then cooled to −10° C. before the addition of lithium bis(trimethylsilyl)amide (4.8 ml of a 1.0M solution in tetrahydrofuran). The mixture was stirred at −10° C. for 30 minutes and a solution of diethylchlorophosphate (0.345 ml) was added. The mixture was stirred at −10° C. for 15 minutes and then 3-(5-fluoropyrimidin-2-yl)propanal (0.334 g) was added, stirred at −10° C. for a further 30 minutes. The mixture was allowed to warm to room temperature and then was washed with aqueous ammonium chloride and extracted with ethyl acetate. The organic layers were dried over $Na_2SO_4$.

Purification of the residue on silica eluting with 70% ethyl acetate 30% hexane afforded a 6:4 mixture of 2-((E)-4-[4-(5-chloropyridin-2-yl)piperazino]sulfonylbut-3-enyl)-5-fluoropyrimidine and 2-((Z)-4-[4-(5-chloropyridin-2-yl)piperazino]sulfonylbut-3-enyl)-5-fluoropyrimidine (0.44 g).

$^1$H NMR ($CDCl_3$): 8.55 (d, 1H), 8.48, (s, 1H), 7.46, (dd, 1H), 6.85, (m, 1H), 6.60, (d, 1H), *6.45, (m, 1H), 6.15, (d, 1H), *6.03, (d, 1H), 3.61, (m, 4H), 3.28, (m, 2H), 3.15, (m, 4H), *2.81, (m, 2H); MS (ES+): 412.3(MH$^+$).

* Denotes minor isomer.

(ii) To a solution of 2-((E)-4-[4-(5-chloropyridin-2-yl)piperazino]sulfonylbut-3-enyl)-5-fluoropyrimidine and 2-((Z)-4-[4-(5-chloropyridin-2-yl)piperazino]sulfonylbut-3-enyl)-5-fluoropyrimidine (0.44 g), in tetrahydrofuran (5 ml), was added hydroxylamine (1.0 ml, 50% aqueous solution). The mixture was stirred for 18 hours and then diluted with EtOAc(10 ml) and washed with saturated ammonium chloride solution(10 ml. The organic layer was dried over $Na_2SO_4$ and evaporated in vacuo to give 2-[4-[4-(5-chloropyridin-2-yl)piperazino]sulfonyl-3-(hydroxyamino)butyl]-5-fluoropyrimidine(0.483 g).

$^1$H NMR ($CDCl_3$): 8.45 (s, 2H), 8.08 (d, 1H), 7.39 (dd, 1H), 6.55 (d, 1H), 5.76 (bs, 2H), 3.59 (m, 4H), 3.46 (m, 1H), 3.42 (m, 2H), 3.33 (m, 4H), 3.10 (m, 4H), 2.82 (m, 1H), 2.15 (m, 1H), 2.01 (m, 1H); MS (ES+): 445.3(MH$^+$).

EXAMPLE 3

The following compounds were prepared

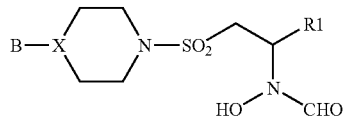

| B | X | R1 | mpt | M + H | Prepared using method in Example |
|---|---|---|---|---|---|
| 5-Cl-2-Pyridyl | N | 1,5,5-trimethyl-3-hydantoinCH2CH2 |  | 517.3 | 2 |
| (5-Cl-2-pyridyl)oxy | C | 4-Cl-phenyl |  | 474.3 | 1 |
| 5-Cl-2-Pyridyl | N | 3,5,5-trimethyl-1-hydantoinCH2CH2 |  | 517.3 | 1 |
| (5-Cl-2-pyridyl)oxy | C | 2-PyrimidinylCH2 |  | 470.3 | 1 |
| 5-Cl-2-Pyridyl | N | 2-pyrimidine-SCH2CH2 |  | 487 | 1 |
| (5-Br-2-pyridyl)oxy | C | 2-PyrimidinylCH2CH2CH2 |  | 528.2 | 1 |
| 5-Cl-2-Pyridyl | N | 3-(OCH2Ph)—Ph |  | 531 | 1 |
| 3,4-diCl-phenyl | N | 2-PyrimidinylCH2CH2 |  | 502 | 1 |
| 4-Cl-phenyl | N | 2-PyrimidinylCH2CH2CH2 |  | 468 | 1 |
| 5-Cl-2-Pyridyl | N | 3-CF3—Ph |  | 493 | 1 |
| 4-Cl-phenyl | N | 3-Pyridyl |  | 397.4 | 2 |
| 5-Cl-2-Pyridyl | N | 4-CF3—Ph |  | 493 | 1 |
| 5-Cl-2-Pyridyl | N | 3-Thiophenyl |  | 431 | 1 |
| 5-Cl-2-Pyridyl | N | 2-PyrazinylCH2CH2CH2 |  | 469 | 2 |
| 5-Cl-2-Pyridyl | N | 2-PyrazinylCH2CH2 |  | 455.4 | 2 |
| 3-Cl-phenyl | N | 2-PyrimidinylCH2CH2 |  | 468.4 | 2 |
| 6-Me-4-pyrimidinyl | N | 2-PyrimidinylCH2CH2CH2 |  | 450.5 | 2 |
| 5-cyano-2-pyridyl | N | 2-PyrazinylCH2CH2CH2 |  | 460.5 | 2 |
| 5-cyano-2-pyridyl | N | 2-PyrazinylCH2CH2 |  | 446.5 | 2 |
| 4-F—Ph | N | 2-PyrimidinylCH2CH2 |  | 438 | 1 |
| 5-CF3-2-Pyridyl | N | 2-PyrimidinylCH2CH2 |  | 489 | 1 |
| 5-cyano-2-pyridyl | N | 2-PyrimidinylCH2CH2 |  | 446 | 1 |
| 5-CF3-2-Pyridyl | N | 2-PyrimidinylCH2CH2CH2 |  | 503 | 1 |
| 5-Cl-2-Pyridyl | N | 4-PyrimidinylCH2CH2CH2 |  | 469 | 1 |
| 4-F—Ph | C | 2-PyrimidinylCH2CH2CH2 |  | 451 | 2 |
| 4-F—Ph | C | 2-PyrimidinylCH2CH2 |  | 437 | 2 |
| 5-Cl-2-Pyridyl | N | 2-(4-MeO-Pyrimidinyl)CH2CH2 |  | 485 | 2 |
| 5-Cl-2-Pyridyl | C | 2-PyrimidinylCH2CH2CH2 |  | 468 | 2 |
| 5-Cl-2-Pyridyl | C | 2-PyrimidinylCH2CH2 |  | 454 | 2 |
| 5-Cl-2-Pyridyl | N | 2-(4-CF3-Pyrimidinyl)-CH2CH2 |  | 523 | 2 |
| 5-Cl-2-Pyridyl | N | 2-(5-Ethyl-Pyrimidinyl)CH2CH2 |  | 483 | 2 |
| 5-Cl-2-Pyridyl | N | 2-(4-MeO-Pyrimidinyl)CH2CH2CH2 |  | 499 | 2 |
| 5-cyano-2-pyridyl | N | 2-(4-MeO-Pyrimidinyl)CH2CH2CH2 |  | 490 | 2 |
| 5-Cl-2-Pyridyl | N | 2-(5-F-Pyrimidinyl)CH2CH2CH2 |  | 487 | 2 |
| 5-Br-2-Pyridyl | N | 2-(4CF3-Pyrimidinyl)CH2CH2CH2 |  | 583 | 2 |
| 5-Cl-2-Pyridyl | N | 2-(4CF3-Pyrimidinyl)CH2CH2CH2 |  | 537 | 2 |
| 5-cyano-2-pyridyl | N | 2-(4CF3-Pyrimidinyl)CH2CH2CH2 |  | 528 | 2 |
| 5-Cl-2-Pyridyl | N | 2-(5-Ethyl-Pyrimidinyl)CH2CH2CH2 |  | 497 | 2 |
| 5-Br-2-Pyridyl | N | 2-(5-Ethyl-Pyrimidinyl)CH2CH2CH2 |  | 541/543 | 2 |
| 5-cyano-2-pyridyl | N | 2-(5-Ethyl-Pyrimidinyl)CH2CH2CH2 |  | 488 | 2 |
| 4-F—Ph | N | PhSO2NHCH2CH2 |  | 515 | 1 |
| 5-Cl-2-Pyridyl | C | PhCH(Me)CH2 | 64–65 |  | 2 |
| 4-F—Ph | N | 1,5,5-trimethyl-3-hydantoinCH(Me)CH2 | 85 |  | 1 |
| 4-F—Ph | N | 4-MeO—PhCH(Me)CH2 |  | 480 | 1 |
| 4-F—Ph | N | 3-MeO—PhCH(Me)CH2 |  | 480 | 1 |
| 4-F—Ph | C | 1,5,5-trimethyl-3-hydantoinCH(Me)CH2 | 77–79 |  | 1 |
| 4-Cl—Ph | N | 3-Cl—PhCH(Me)CH2 |  | 500, 502 | 1 |
| 6-Cl-2-pyrimidinyl | N | 2-pyrazinylCH(Me)CH2 | 79–81 | 470 | 1 |
| 5-Cl-2-Pyridyl | N | 2-pyridylCH(Me)CH2 |  | 468 | 2 |
| 5-cyano-2-pyridyl | N | 2-pyridylCH(Me)CH2 |  | 459 | 2 |
| 5-cyano-2-pyridyl | N | 2-pyrazinylCH(Me)CH2 | 80 | 460 | 2 |
| 5-CN-2-Pyridyl | N | 2-PyrimidinylCH2CH2CH2CH2 |  | 474.5 | 1 |
| 4-Cl-Phenyl | N | 2-PyrimidinylCH2CH2CH2CH2 |  | 482.45 | 1 |
| 5-Cl-2-Pyridyl | N | 2-PyrimidinylCH2CH2CH2CH2 |  | 483.4 | 1 |
| 5-Cl-2-Pyridyl | N | 4-Cl-Phenyl |  | 459.3 | 1 |
| 5-F-2-Pyridyl | N | 2-PyrimidinylCH2CH2 |  | 453.2 | 2 |
| 5-F-2-Pyridyl | N | 2-(5-F-Pyrimidinyl)CH2CH2 |  | 457.1 | 2 |
| 5-Br-2-Pyridyl | N | 2-(5-F-Pyrimidinyl)CH2CH2 |  | 517/519 | 2 |
| 4-Cl-Phenyl | N | 2-(5-F-Pyrimidinyl)CH2CH2 |  | 472.1 | 2 |
| 5-CN-2-Pyridyl | N | 2-(5-F-Pyrimidinyl)CH2CH2 |  | 464.18 | 2 |
| 5-CF3-2-Pyridyl | N | 2-(5-F-Pyrimidinyl)CH2CH2 |  | 507.14 | 2 |
| 5-Cl-2-Pyridyl | N | 2-(5-Br-Pyrimidinyl)CH2CH2 |  | 533/535 | 2 |
| 5-F-2-Pyridyl | N | 2-(5-Br-Pyrimidinyl)CH2CH2 |  | 517/519 | 2 |
| 4-F-Phenyl | N | 2-(5-Br-Pyrimidinyl)CH2CH2 |  | 516/518 | 2 |

-continued

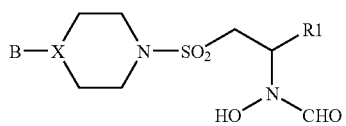

| B | X | R1 | mpt | M + H | Prepared using method in Example |
|---|---|---|---|---|---|
| 5-F-2-Pyridyl | N | 2-(5-Me-Pyrimidinyl)CH2CH2 | | 453.5 | 2 |
| 4-Cl-Phenyl | N | 2-(5-Me-Pyrimdiinyl)CH2CH2 | | 468.4 | 1 |
| 5-Br-2-Pyridyl | N | 2-(5-Me-Pyrimidinyl)CH2CH2 | | 513/515 | 2 |
| 5-CF3-2-Pyridyl | N | 2-(5-Me-Pyrimidinyl)CH2CH2 | | 503.4 | 2 |
| 5-F-2-Pyridyl | N | 2-(4-CF3-Pyrimidinyl)CH2CH2 | | 507.06 | 2 |
| 4-Cl-Phenyl | N | 2-(4-CF3-Pyrimidinyl)CH2CH2 | | 521.9 | 2 |
| 5-CF3-2-Pyridyl | N | 2-(4-CF3-Pyrimidinyl)CH2CH2 | | 556.95 | 2 |
| 5-Br-2-Pyridyl | N | 2-(4-CF3-Pyrimidinyl)CH2CH2 | | 566/568 | 2 |
| 5-Cl-2-PYridyl | N | 2-(5-Cl-Pyrimidinyl)CH2CH2 | | 489/491 | 2 |
| 5-Br-2-Pyridyl | N | 2-(5-Cl-Pyrimidinyl)CH2CH2 | | 532/534 | 2 |
| 5-F-2-Pyridyl | N | 2-(5-Cl-Pyrimidinyl)CH2CH2 | | 473 | 2 |
| 4-F-Phenyl | N | 2-(5-Cl-Pyrimdinyl)CH2CH2 | | 472 | 2 |
| 4-Cl-Phenyl | N | 2-(5-Cl-Pyrimidinyl)CH2CH2 | | 488/490 | 2 |
| 4-Br-2-Pyridyl | N | 2-(5-Br-Pyrimidinyl)CH2CH2 | | 576/578/580 | 2 |
| 4-Cl-Phenyl | N | 2-(5-Br-Pyrimidinyl)CH2CH2 | | 531/533/535 | 2 |
| 5-CN-2-Pyridyl | N | 3-(5-Pyridyl)CH2CH2 | | 479/481 | 2 |
| 4-CF3-Phenyl | N | 2-PyrimidinylCH2CH2CH2 | | 502 | 2 |
| 4-Br-Phenyl | N | 2-(5-F-Pyrimidinyl)CH2CH2 | | 518.3 | 2 |
| 3,4-DiCl-Phenyl | N | 2-(5-F-Pyrimidinyl)CH2CH2 | | 506.34 | 2 |
| 3-Cl-Phenyl | N | 2-(5-F-Pyrimidinyl)CH2CH2 | | 472.38 | 2 |
| 4-CF3-Phenyl | N | 2-(5-F-Pyrimidinyl)CH2CH2 | | 506.4 | 2 |
| 4-F—Ph | N | 2-PyrimidinylCH2CH2 | 87–89 | | 1 |
| 3,4-di-Cl—Ph | N | 2-PyrimidinylCH2CH2 | | 489 | 1 |
| 4-Cl—Ph | N | 2-PyrimidinylCH2CH2 | | 455 | 1 |
| 5-Me-2-Pyridyl | N | 2-PyrimidinylCH2CH2CH2 | | 449 | 1 |
| 5-Me-2-Pyridyl | N | 2-PyrimidinylCH2CH2 | | 435 | 1 |
| 4-F—Ph | N | 2-PyrazinylCH2CH2CH2 | | 452 | 1 |
| 4-F—Ph | N | (6-Cl-2-pyrazinyl)CH2CH2 | 91–92 | | 2 |
| 4-F—Ph | N | 5-F-2-PyrimidinylCH(CH3)CH2 | 143–4 | | 2 |
| 4-Cl—Ph | N | 2-PyrazinylCH(CH3)CH2 | | 468 | 1 |
| 4-F—Ph | C | 5-F-2-PyrimidinylCH(CH3)CH2 | | 469 | 1 |

The starting piperazine and piperidine sulphonamides required for the synthesis of compounds were available commercially or were prepared as shown below:

1-(4-fluorophenyl)-4-(methanesulfonyl)piperazine

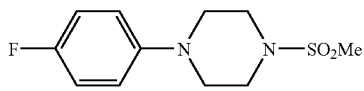

To a solution of 1-(4-fluorophenyl)piperazine (35 g, 194 mmol) and pyridine (17.5 ml) in dry dichloromethane (200 ml) at 0° C. was added methanesulfonyl chloride (20 ml, 258 mmol) dropwise. The mixture was stirred for 3 hours at room temperature. The mixture was washed with water and extracted with dichloromethane (2×100 ml). The organic layers were dried with MgSO4 and evaporated in vacuo. The residue was triturated and washed with methanol to give 1-(4-fluorophenyl)-4-(methanesulfonyl)piperazine (39.35 g) as white crystals.

$^1$H NMR (CDCl$_3$): 7.00 (m, 2H), 6.90 (m, 2H), 3.40 (m, 4H), 3.20 (m, 4H), 2.83 (s, 3H).

The aryl/heteroarylpiperazines and piperidines used as starting materials were commercially available or are described in the scientific literature.

1-(6-chloropyrimidin-4-yl)-4-mesylpiperazine

A mixture of 4,6-dichloropyrimidine (39.4 g), 1-mesylpiperazine hydrochloride (55.7 g) and triethylamine (116 ml) in ethanol (500 ml) was stirred at reflux temperature for 4 hours. The mixture was then stirred at room temperature for 12 hours. The solid, which had separated, was collected by filtration, slurry washed with ethanol (2×80 ml, 160 ml) then with diethyl ether (150 ml), and dried to give 1-(6-chloropyrimidin-4-yl)-4-mesylpiperazine as a cream solid (71.9 g). mp 200–202° C.

NMR (d6-DMSO): 2.88 (s, 3H), 3.18 (m, 4H), 3.80 (m, 4H), 7.04 (s, 1H), 8.38 (m, 1H); m/z 277.3 (M+1).

Using an analogous procedure 1-mesylpiperazine hydrochloride, CAS(161357-89-7), was reacted with the appropriate chloropyridine to give the following, compounds.

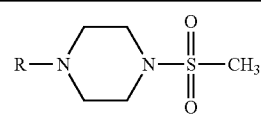

| R | m/z (M + 1) |
|---|---|
| 5-Cl-2-pyridyl | 276 |
| 5-CF$_3$-2-pyridyl | 310 |

| R | m/z (M + 1) |
|---|---|
| 5-CN-2-pyridyl | 267 |
| 5-Br-2-pyridyl | 320/322 |

2-(4-piperidinyloxy)-5-chloropyridine i) NaH (2.88 g, 66 mmol, 55% dispersion in mineral oil) was stirred in dry DME (200 ml), under Argon. A mixture of 2,5-dichloropyridine (8.87 g, 60 mmol) and 4-hydroxypiperidine (6.67 g, 66 mmol) dissolved in dry DME (200 ml) was added to the NaH suspension dropwise, over a period of 30 minutes. After complete addition the reaction is heated to 82° C. for 48 hrs, maintaining the Argon blanket. The reaction was slowly quenched with water before removing most of the THF. Extracted the aqueous with DCM (×3). The organic layers were dried with $Na_2SO_4$ and evaporated in vacuo to afford 2-(4-piperidinyloxy)-5-chloropyridine as a yellow oil (12.7 g, quantitative).

$^1$H NMR (DMSO): 8.17 (d, 1H), 7.76 (dd, 1H), 6.81 (d, 1H), 4.96 (m, 1H), 2.93 (m, 2H), 2.53 (m, 2H), 1.91 (m, 2H), 1.46 (m, 2H); MS (ES+): 213.3 (MH$^+$), 225.3 (MNa$^+$).

In an analogous manner 2-(4-piperidinyloxy)-5-bromopyridine was prepared MH+257.3

EXAMPLE 4

Resolution

N-[(1S)-1-({[4-(5-chloropyridin-2-yl)piperazino]sulfonyl}methyl)-4-(pyrimidin-2-yl)butyl]-N-hydroxyformamide

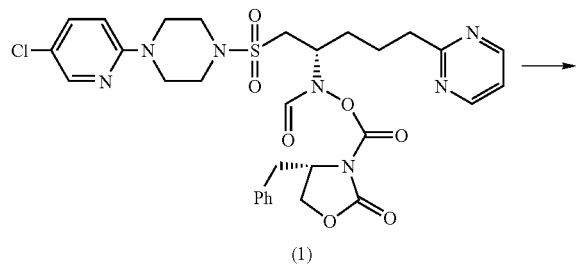

(1)

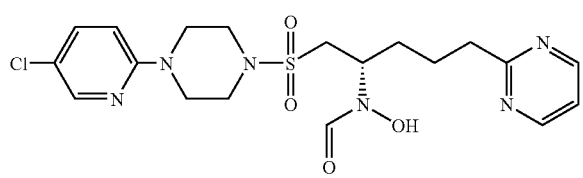

To the carbamate 1 (3.8 g, 5.66 mmol) dissolved in THF (76 ml) was added methanol (76 ml), followed by water (38 ml), and to this solution was added lithium hydroxide monohydrate (2.37 g, 56.6 mmol). After stirring for 2 hours at room temperature the solvents were removed under reduced pressure and the residue dissolved in water (250 ml), washed with ethyl acetate (200 ml) and diethylether (2×250 ml). Saturated aqueous ammonium chloride was added until the aqueous layer was approximately pH 8 and it was then extracted with dichloromethane (3×250 ml). The combined dichloromethane extracts were dried (MgSO$_4$) and evaporated to give the product as a white powder (2.2 g, 83%). Chiral HPLC using a Chiralpak AS column showed the product had been isolated in 96% ee (believed to have S stereochemistry). Mpt (from EtOH) 124.5–126.5° C.;

$[\alpha]_D^{25}$=–17.2 (MeOH); NMR CDCl$_3$ d 9.9 (br s, 1H)*; 8.7 (m, 2H); 8.5 (s, 1H)*; 8.1 (br s, 1H); 8.0 (s, 1H)*; 7.5 (dd, 1H); 7.2 (m, 1H); 6.6 (d, 1H); 4.9 (m, 1H)*; 4.2 (m, 1H)*; 3.7–3.5 (m, 4H); 3.5 (m, 1H)*; 3.4–3.2 (m, 4H); 3.3 (m, 1H)*; 3.1–2.9 (m, 3H); 2.0–1.6 (m, 4H). MS for C$_{19}$H$_{25}$ClN$_6$O$_4$S (M+H) calcd 469. found 469.

* rotameric signals

Step A

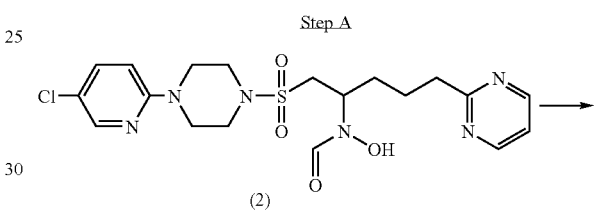

(2)

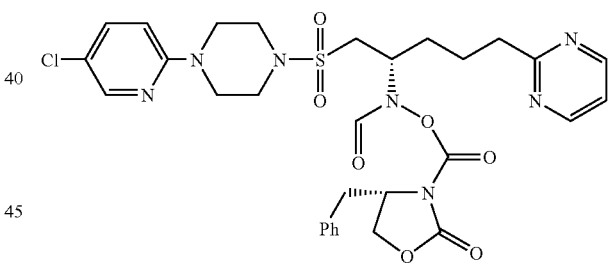

To the reverse hydroxamate 2 (18.76 g, 40 mmol) dissolved in dichloromethane (300 ml) and cooled to 0° C. was added triethylamine (10.4 ml, 75mmol) followed by (4S)-4-Benzyl-2-oxazolidinone-3-carbonyl chloride (10.55 g, 44 mmol)[CAS number 139149-49-8]. After stirring for 3 hours at −3–0° C. the mixture was washed with water (250 ml), dried (MgSO4), and evaporated to give a beige foam (27.1 g). The diastereomers were separated using preparative hplc eluting with ethyl acetate/EtOH (5%). The more polar diastereomer was isolated in 35% yield. MS for C$_{30}$H$_{34}$ClN$_7$O$_7$S (M+H) calcd 672. found 672.

Compound 2 was prepared using the methods given in Example 2: (M+H 469), mpt 131–134° C.; NMR (DMSO) 9.8 (1H, br), 8.7 (2H, m), 8.3 and 7.9 (1H, s), 8.1 (2H, s), 7.6 (1H, m), 6.9(1H, m), 4.1 (1H, m), 3.6 (4H, m), 3.2 (6H, m), 2.8 (2H, m), 1.8 (4H, m).

EXAMPLE 5

In an analogous manner to that given in Example 4 the following compounds were produced:

N-[(1S)-1-({[4-(5-bromopyridin-2-yl)piperazino]sulfonyl}methyl)-4-(pyridin-2-yl)butyl]-N-hydroxyformamide

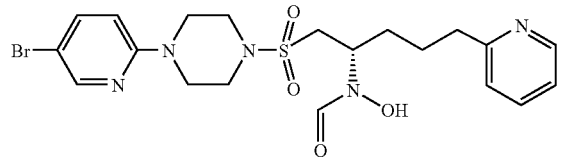

NMR CDCl$_3$ d 11.9 (br s, 1H)*; 8.5 (s, 1H)*; 8.5–8.4 (m, 1H); 8.2 (m, 1H); 8.1 (s, 1H)*; 7.8–7.7 (m, 1H); 7.6 (m, 1H); 7.3–7.2 (m, 2H); 6.6 (m, 1H); 5.0–4.9 (m, 1H)*; 4.3–4.2 (m, 1H)*; 3.7–3.6 (m, 4H); 3.6 (m, 1H)*; 3.4–3.3 (m, 4H); 3.3 (m, 1H)*; 3.1 (dd, 1H)*, 2.9 (m, 1H)*, 2.9–2.8 (m, 2H); 2.1–1.6 (m, 4H). MS for C$_{20}$H$_{26}$BrN$_5$O$_4$S (M+H) calcd 514. found 514. [a]$_D^{25}$=−14 (c=2.3, MeOH)

* rotameric signals

The racemic starting material was prepared using the method given in Example 2. M+H=512/514.

N-[(1S-1-({[4-(5-chloropyridin-2-yl)piperazino]sulfonyl}methyl)-3-(5-fluoropyrimidin-2-yl)propyl]-N-hydroxyformamide

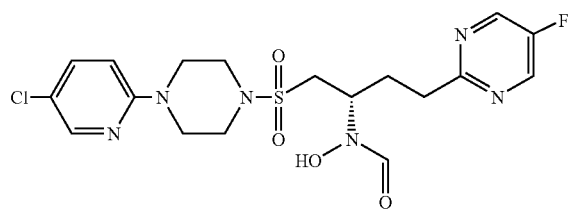

$^1$H NMR (DMSO, 373K): 9.44 (br s, 1 H), 8.70 (s, 2 H), 8.10 (d, 1 H, J=2.6 Hz), 8.05 (br s, 1 H), 7.57 (dd, 1 H, J=9.1, 2.6 Hz), 6.86 (d, 1 H, J=9.1 Hz), 4.40 (br s, 1 H), 3.59 (dd, 4 H, J=5.3, 5.0 Hz), 3.47 (dd, 1 H, J=14.6, 7.4 Hz), 3.28 (dd, 4 H, J=5.3, 5.0 Hz), 3.24 (dd, 1 H, J=14.6, 4.3 Hz), 2.93 (m, 2 H), 2.16 (m, 2 H). MS (ESI): 473 (MH$^+$). a$_d$=−11.03 (MeOH, c=1.242).

The racemic starting material was prepared in Example 2.

N-[(1S)-1-({[4-(4-fluorophenyl)piperazino]sulfonyl}methyl)-4-(pyrimidin-2-yl)butyl]-N-hydroxyformamide

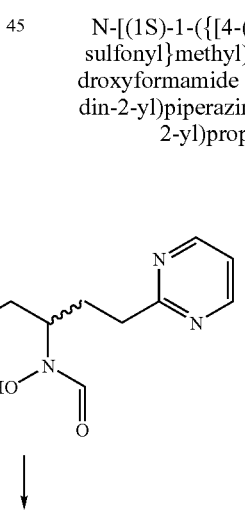

M+H 452.44; NMR CDCl$_3$ d 9.9 (br s, 1H)*; 8.7 (m, 2H); 8.5 (s, 1H)*; 8.05 (s, 1H)*; 7.2 (m, 1H); 7.0–6.9 (m, 4H); 4.9 (m, 1H)*; 4.2 (m, 1H)*; 3.5–3.4 (m, 4H); 3.5 (m, 1H)*; 3.2–3.1 (m, 4H); 3.3 (m, 1H)*; 3.1–2.9 (m, 3H); 2.0–1.6 (m, 4H).

* rotameric signals

The racemic starting material was prepared using the method given in Example 3. NMR (DMSO) 10.0 (1H, br s), 8.6 (2H, m), 8.2 (1H, d), 7.2 (1H, m), 6.9 (4H, m), 4.9 and 4,2 (1H, br), 3.4 (6H, m), 3.0 (6H, m), 1.9 (4H, m).

EXAMPLE 6

Chromatographic Resolution

N-[(1S)-1-({[4-(5-chloropyridin-2-yl)piperazino]sulfonyl}methyl)-3-(pyrimidin-2-yl)propyl]-N-hydroxyformamide and N-[(1R)-1-({[4-(5-chloropyridin-2-yl)piperazino]sulfonyl}methyl)-3-(pyrimidin-2-yl)propyl]-N-hydroxyformamide

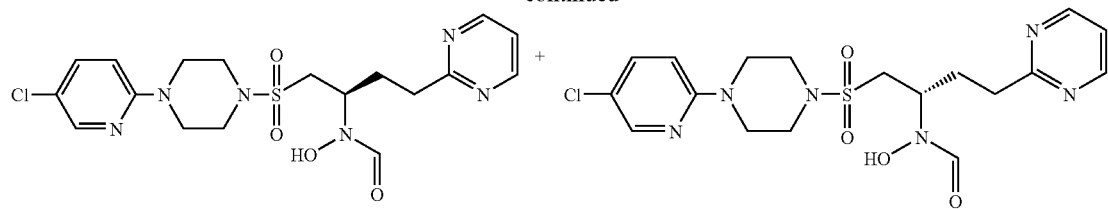

N-[1-({[4-(5-chloropyridin-2-yl)piperazino]sulfonyl}methyl)-3-(pyrimidin-2-yl)propyl]-N-hydroxyformamide prepared in a racemic form was separated into single enantiomer forms by chromatographic separation on a column packed with Chiralpak AD No. AD00CJ-HK002 and eluted with ethanol. Biological activity lies in the compound eluted second from the column—assumed to have S stereochemistry.

1$^{st}$ enantiomer eluted MH+455.

2$^{nd}$ enantiomer eluted MH+455.

The racemic starting material was prepared using the method given in Example 2.

MH+=455. NMR (DMSO) 9.9, 9.6 (1H br s), 8.6 (2H, m), 8.3 and 7.9 (1H, s), 8.1 (1H, dd), 7.3 (1H, m), 6.9 (1H, d), 4.7 and 4.2 (1H, broad m), 3.6 (4H, m), 3.4–3.2 (6H, m), 2.8 (2H, m), 2.1 (2H, m).

EXAMPLE 7

Further Examples of Chromatographic Resolution

The following compounds were resolved using the conditions given in Example 6:

N-[(1S)-1-({[4-(5-trifluoromethylpyridin-2-yl)piperazino]sulfonyl}methyl)-3-(pyrimidin-2-yl)propyl]-N-hydroxyformamide and N-[(1R)-1-({[4-(5-trifluoromethylpyridin-2-yl)piperazino]sulfonyl}methyl)-3-(pyrimidin-2-yl)propyl]-N-hydroxyformamide

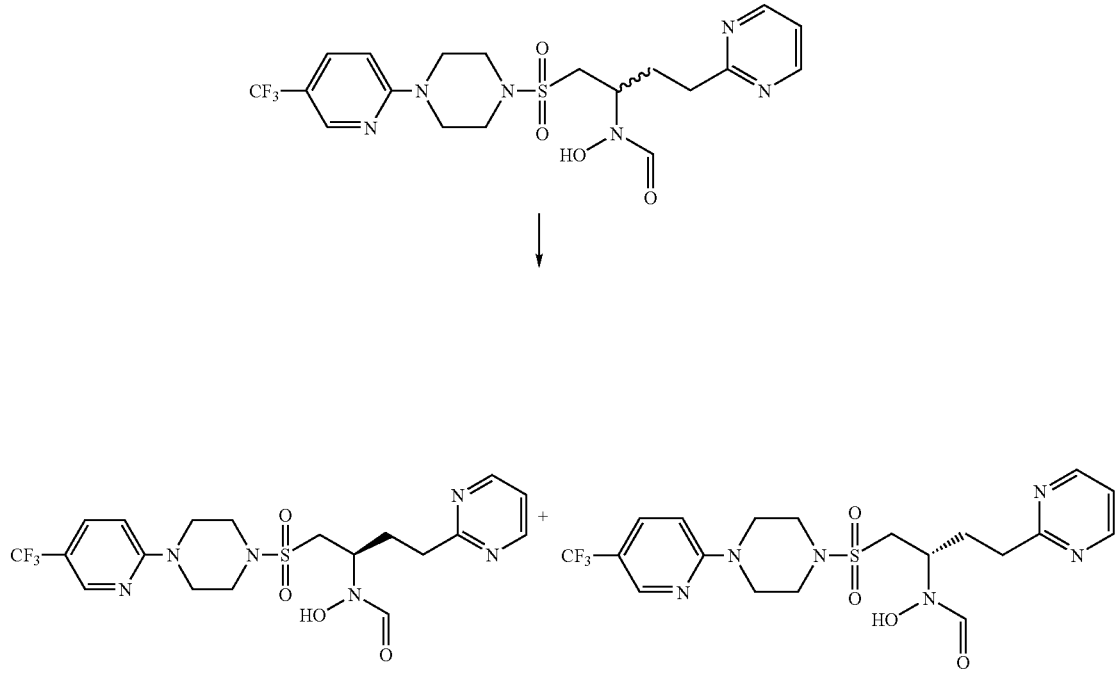

1$^{st}$ enantiomer eluted M+H 489.5.
2$^{nd}$ enantiomer eluted M+H 489.5.

The racemic starting material was prepared in Example 3.

N-[(1S)-1-({[4-(5-bromopyridin-2-yl)piperazino]sulfonyl}methyl)-4-(pyrimidin-2-yl)butyl]-N-hydroxyformamide and N-[(1R)-1-({[4-(5-bromopyridin-2-yl)piperazino]sulfonyl}methyl)-4-(pyrimidin-2-yl)butyl]-N-hydroxyformamide

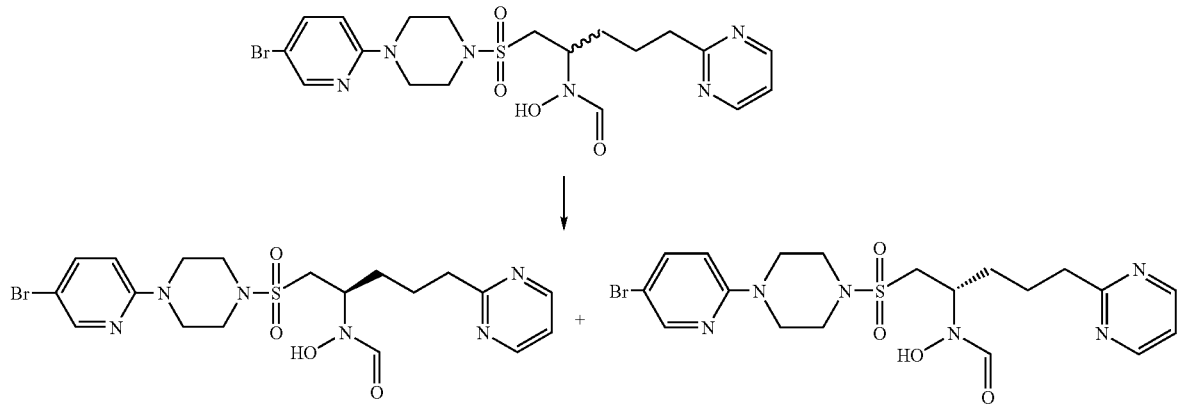

1$^{st}$ enantiomer eluted M+H 513/515.
2$^{nd}$ enantiomer eluted M+H 513/515.

The racemic starting material was prepared using the method outlined in Example 2: M+H 513/515.

EXAMPLE 8

The following compounds were prepared

| B | X | R1 | mpt | M + H | Prepared using method in Example |
|---|---|---|---|---|---|
| (5-Cl-2-pyridyl)oxy | C | 2-PyrimidinylCH2CH2CH2 (S enantiomer) | | 484 | 4 |
| 5-CF3-2-Pyridyl | N | 2-PyrimidinylCH2CH2CH2 (S enantiomer) | 141–142 | 503 | 4 |
| 4-F-Phenyl | N | 2-(5-F-Pyrimidinyl)CH2CH2 (S enantiomer) | | 456.24 | 6** |
| 4-F-Phenyl | N | 2-(5-F-Pyrimidinyl)CH2CH2 | | 456.2 | 2 |
| 4-Br—Ph | N | 2-PyrazinylCH(CH3)CH2 mixed diastereomers 3:1 (A:B) | | 512 | 1 |
| 4-Cl—Ph | C | 2-PyrazinylCH(CH3)CH2 Diastereomer A | | 467 | 1 |
| 4-Cl—Ph | C | 2-PyrazinylCH(CH3)CH2 mixed diastereomers 1:2 (A:B) | | 467 | 1 |
| 4-Br—Ph | C | 2-PyrazinylCH(CH3)CH2 mixed diastereomers 3:1 (A:B) | | 511 | 1 |
| 5-Cl-2-Pyridyl | N | 5-F-2-PyrimidinylCH(CH3)CH2 mixed diastereomers 1:2 (A:B) | | 487 | 1 |
| 4-Cl—Ph | N | 5-F-2-PyrimidinylCH(CH3)CH2 Diastereomer A | 157–9 | | 1 |
| 4-Cl—Ph | N | 5-F-2-PyrimidinylCH(CH3)CH2 Diastereomer B | 164–7 | | 1 |
| 4-Br—Ph | N | 5-F-2-PyrimidinylCH(CH3)CH2 Diastereomer A | 167–9 | | 1 |
| 4-Br—Ph | N | 5-F-2-PyrimidinylCH(CH3)CH2 Diastereomer B | 183–5 | | 1 |
| 4-Cl—Ph | C | 5-F-2-PyrimidinylCH(CH3)CH2 Diastereomer A | 195–8 | | 1 |
| 4-Cl—Ph | C | 5-F-2-PyrimidinylCH(CH3)CH2 Diastereomer B | 155–8 | | 1 |
| 3,4-di-Cl—Ph | N | 5-F-2-PyrimidinylCH(CH3)CH2 Diastereomer A | 172–3 | | 1 |
| 3,4-di-Cl—Ph | N | 5-F-2-PyrimidinylCH(CH3)CH2 Diastereomer B | 172–3 | | 1 |
| 5-CN-2-Pyridyl | N | 5-F-2-PyrimidinylCH(CH3)CH2 Diastereomer A | | 478 | 1 |
| 4-F—Ph | N | (S) 5-F-2-PyrimidinylCH(CH3)CH2 (S enantiomer) | | 470 | 7 |
| 4-F—Ph | N | (R,S)-PyrazinylCH(CH3)CH2 (S enantiomer) | | 452 | 4 |

In the above Table:
** indicates the compound (S enantiomer) prepared by the method in Example 6 using column Chiralpak AD (250 mm×4.6 mm) No. ADooCE-JJ122 and eluent MeOH/MeCN 15/85;

Diastereomers A and B refer to the order of elution from a silica column eluted with 3–5% ethanol in dichloromethane (diastereomer A is the first fraction to elute, diastereomer B the second).

EXAMPLE 9

We provide NMR data for the following compounds listed in Example 8:

N-[(1S-1-({[4-(5-trifluoromethylpyridin-2-yl)piperazino]sulfonyl}methyl)-4-(pyrimidin-2-yl)butyl]-N-hydroxyformamide

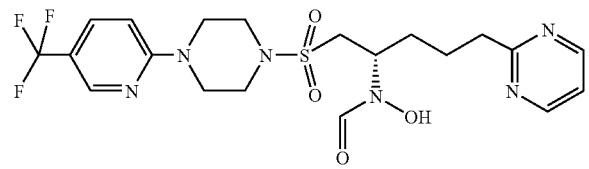

NMR CDCl$_3$ δ 10.1 (br s, 1H)*; 8.7 (m, 2H); 8.5 (s, 1H)*; 8.4 (br s, 1H); 8.1 (s, 1H)*; 7.7 (dd, 1H); 7.2 (m, 1H); 6.7 (d, 1H); 4.9 (m, 1H)*; 4.2 (m, 1H)*; 3.9–3.7 (m, 4H); 3.6 (m, 1H)*; 3.4–3.2 (m, 4H); 3.3 (m, 1H)*; 3.1–2.9 (m, 3H); 2.0–1.6 (m, 4H).
* rotameric signals.

N-({[4-fluorophenylpiperazino]sulphonyl}methyl)-3-[(5-fluoropyrimidin-2-yl)propyl]-N-hydroxyformamide

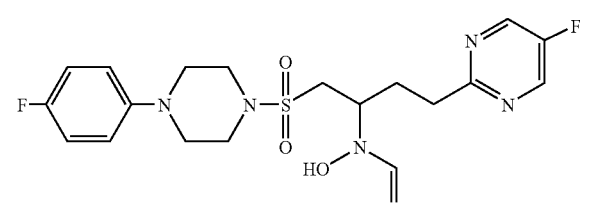

$^1$H NMR (DMSO, 373K): 9.46 (br s, 1 H), 8.73 (s, 2 H), 7.08–6.96 (m, 4H), 4.42 (br s, 1H), 3.50 (dd, J=14.8, 7.5 Hz, 1H), 3.35 (m, 4H), 3.28 (dd, J=14.8, 4.4 Hz, 1H), 3.18 (m, 4H), 2.97 (m, 2H), 2.21 (m, 2H).

N-[(1R or 1S)-({[4-chlorophenylpiperazino] sulphonyl}methyl)-3-[(3R or 3S)-(5-fluoropyrimidin-2-yl)butyl]-N-hydroxyformamide (single diastereomer A)

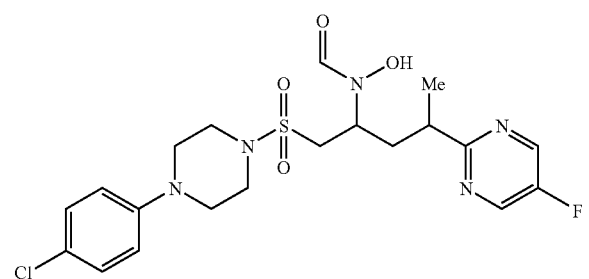

1H NMR (CDCl3) (2 rotamers in approximately equal proportions): 8.72 (s, 0.5H), 8.57 (d, 2H), 8.25 (s, 0.5H), 7.89 (s, 0.5H), 7.23 (dd, 2H), 6.83 (dd, 2H), 4.94 (sext, 0.5H), 4.30 (m, 0.5H), 3.57 (dd, 0.5H), 3.44 (m, 2H), 3.37 (m, 2.5H), 3.16 (m, 5.5H), 3.02 (dd, 0.5H), 2.52 (ddd, 0.5H), 2.35 (ddd, 0.5H), 2.02 (dt, 0.5H), 1.89 (ddd, 0.5H), 1.40 (dd, 3H);

N-[(1R or 1S)-({[4-bromophenylpiperazino] sulphonyl}methyl)-3-[(3R or 3S)-(5-fluoropyrimidin-2-yl)butyl]-N-hydroxyformamide (single diastereomer A)

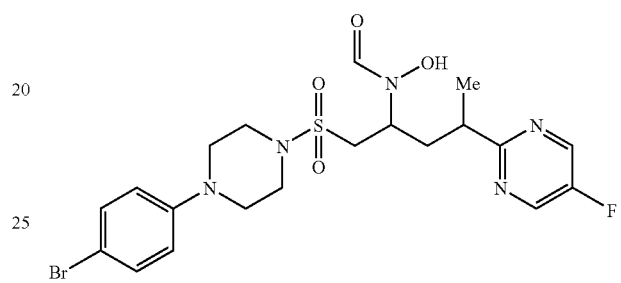

$^1$H NMR (CDCl3) (2 rotamers in approximately equal proportions): 8.72 (s, 0.5H), 8.57 (d, 2H), 8.25 (s, 0.5H), 7.89 (s, 0.5H), 7.38 (dd, 2H), 6.80 (dd, 2H), 4.94 (sext, 0.5H), 4.30 (m, 0.5H), 3.57 (dd, 0.5H), 3.44 (m, 2H), 3.37 (m, 2.5H), 3.16 (m, 5.5H), 3.02 (dd, 0.5H), 2.52 (ddd, 0.5H), 2.35 (ddd, 0.5H), 2.02 (dt, 0.5H), 1.89 (dt, 0.5H), 1.40 (dd, 3H);

N-[(1R or 1S)-({[4-chlorophenylpiperidino] sulphonyl}methyl)-3-[(3R or 3S)-(5-fluoropyrimidin-2-yl)butyl]-N-hydroxyformamide (single diastereomer A)

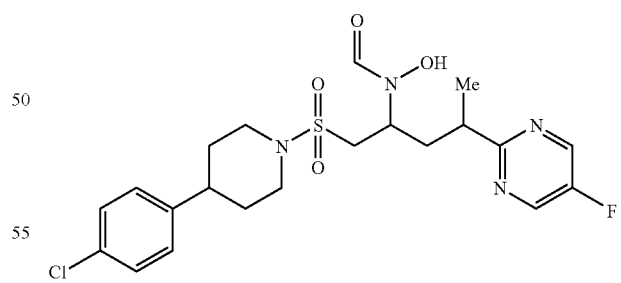

1H NMR (CDCl3) (2 rotamers in approximately equal proportions): 8.69 (s, 0.5H), 8.57 (d, 2H), 8.25 (s, 0.5H), 7.89 (s, 0.5H), 7.27 (obscured), 7.13 (dd, 2H), 4.91 (sext, 0.5H), 4.30 (m, 0.5H), 3.87 (m, 2H), 3.57 (dd, 0.5H), 3.35 (dd, 0.5H), 3.18 (m, 1.5H), 3.00 (dd, 0.5H), 2.85 (m, 2H), 2.55 (m, 1.5H), 2.35 (ddd, 0.5H), 2.06 (dt, 0.5H), 1.88 (m, 2.5H), 1.7 (obscured), 1.40 (dd, 3H);

N-[(1R or 1S)-({[3,4-dichlorophenylpiperazino]sulphonyl}methyl)-3-[(3R or 3S)-(5-fluoropyrimidin-2-yl)butyl]-N-hydroxyformamide (single diastereomer A)

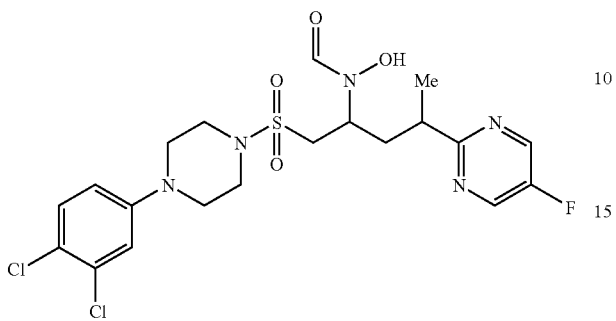

1H NMR (CDCl3) (2 rotamers in approximately equal proportions): 8.62 (s, 0.5H), 8.55 (d, 2H), 8.22 (s, 0.5H), 7.86 (s, 0.5H), 7.28 (m, 1H), 6.95 (m, 1H), 6.73 (m, 1H), 4.92 (sext, 0.5H), 4.30 (m, 0.5H), 3.57 (dd, 0.5H), 3.44 (m, 2H), 3.37 (m, 2.5H), 3.16 (m, 5.5H), 3.02 (dd, 0.5H), 2.52 (ddd, 0.5H), 2.37 (ddd, 0.5H), 2.04 (dt, 0.5H), 1.89 (dt, 0.5H), 1.40 (dd, 3H);

N-[(1R or 1S)-({[4-(5-cyanopyridin-2-yl)piperazino]sulphonyl}methyl)-3-[(3R or 3S)-(5-fluoropyrimidin-2-yl)butyl]-N-hydroxyformamide (single diastereomer A)

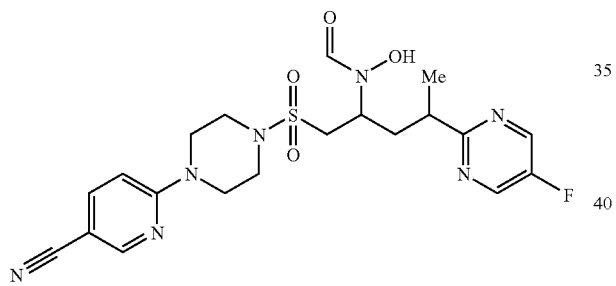

1H NMR (CDCl3) (2 rotamers in approximately equal proportions): 8.72 (s, 0.5H), 8.55 (s, 2H), 8.41 (s, 1H), 8.22 (s, 0.5H), 7.86 (s, 0.5H), 7.65 (m, 1H), 6.61 (dd, 1H), 4.92 (m, 0.5H), 4.30 (m, 0.5H), 3.78 (m, 4H), 3.57 (dd, 0.5H), 3.38 (m, 2H), 3.30 (m, 2.5H), 3.16 (m, 1.5H), 3.02 (dd, 0.5H), 2.52 (m, 0.5H), 2.37 (m, 0.5H), 2.04 (dt, 0.5H), 1.84 (dt, 0.5H), 1.40 (dd, 3H);

N-[(1S-({[4-(4-fluorophenylpiperazino]sulphonyl}methyl)-3-[(3S)-(5-fluoropyrimidin-2-yl)butyl]-N-hydroxyformamide

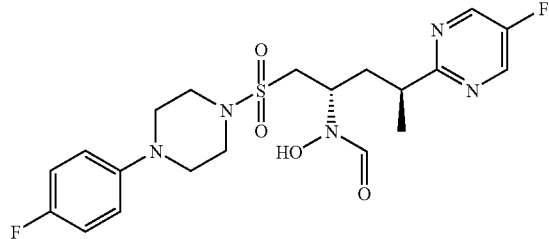

1H NMR (DMSO-d6): 9.9, 9.53 (2s, 1H), 8.78 (s, 2H), 7.98 (d, 1H), 7.12–6.91 (m, 4H), 4.8, 4.17 (2s, 1H), 3.13 (m, 4H), 3.0 (m, 1H), 1.86 (m, 1H), 1.22 (m, 3H).

EXAMPLE 10

1-({[4-(4-chlorophenyl)piperazin-1-yl]sulfonyl}methyl)-3-(5-chloropyridin-3-yl)propyl(hydroxy)formamide

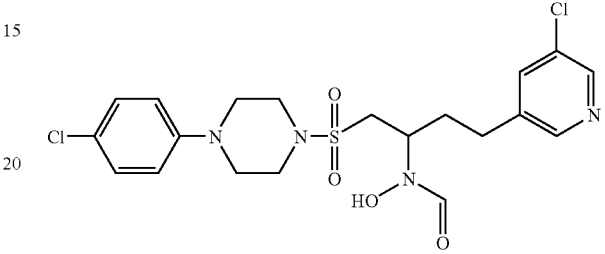

To formic acid (400 μl, 10.8 mmol) at 0° C. was added acetic anhydride (102 μl, 1.1 mmol) and the mixture was then stirred at RT for 15 minutes. The mixture was then re-cooled to 0° C., and a solution of 1-(4-chlorophenyl)-4-{[4-(5-chloropyridin-3-yl)-2-(hydroxyamino)butyl]sulfonyl}piperazine (100 mg, 0.22 mmol) in THF was added dropwise via syringe. After stirring at RT for 1.5 hours, volatiles were removed in vacuo, and the residue was azeotroped with toluene (2 mL). The residue was then dissolved in methanol (5 mL) and stirred at 40° C. for 1 hour. After cooling to RT, the solvent was evaporated, and the residue dissolved in methanol (0.5 mL). Diethyl ether (5 mL) was then added and the cloudy suspension stirred at RT for 1 hour. The solid that precipitated was filtered, washed with diethyl ether and dried in vacuo, to give the title compound as an off-white solid (48 mg, 0.099 mmol).

$^1$H NMR (DMSO, 373K): 9.55 (br s, 1 H), 8.43 (d, 1 H); 8.41 (d, 1 H), 8.17 (br s, 1H), 7.76 (dd, 1 H), 7.25 (m, 2 H), 6.96 (m, 2H), 4.35 (br s, 1H), 3.49 (dd, 1 H), 3.34 (m, 4 H), 3.25 (m, 5 H), 2.67 (m, 2 H), 2.02 (m, 2 H). MS (ESI): 487.06, 489.04, 490.08 (MH$^+$ 2×Cl).

The starting material was prepared as follows:

(i) ethyl 3-(5-chloropyridin-3-yl)propanoate

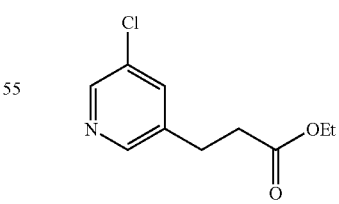

To a stirred solution of ethyl (2E)-3-(5-chloropyridin-3-yl)prop-2-enoate (338 mg, 1.6 mmol) [CAS number 163083-45-2] in dry ethanol (10 mL) at 0° C. under an atmosphere of argon was added solid sodium borohydride (67 mg, 1.75 mmol). The reaction mixture was allowed to warm to room temperature and stirred for four hours, whereupon additional sodium borohydride (67 mg, 1.75 mmol) was added. After stirring for an additional eighteen hours, saturated aqueous ammonium chloride solution (5 mL) was added. Volatiles were removed in vacuo, and the residue partitioned between water (10 mL) and ethyl acetate (10 mL). The layers were separated and the aqueous phase extracted with ethyl acetate (3×10 mL). The combined organic extracts were then dried (MgSO$_4$), filtered and concentrated in vacuo. Flash chromatography (silica gel, 20% to 100% ethyl acetate in hexane) gave the title compound (132 mg, 0.62 mmol) and the saturated alcohol (70 mg).

$^1$H NMR (CDCl$_3$): 8.43 (m, 1 H), 8.34 (m, 1H), 7.55 (m, 1H), 4.16 (q, 2H), 2.96 (dd, 2H), 2.63 (dd, 2H).

(ii) 1-{[4-(4-chlorophenyl)piperazin-1-yl]sulfonyl}-4-(5-chloropyridin-3-yl)butan-2-one

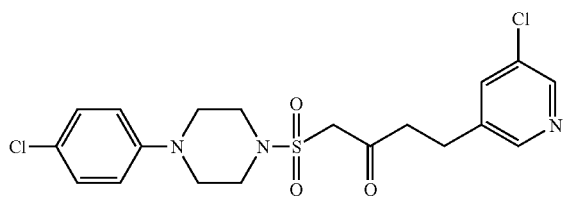

To a stirred solution of 1-(4-chlorophenyl)-4-(methylsulfonyl)piperazine (235 mg, 0.85 mmol) in dry THF (7.5 mL) at −10° C. under an argon atmosphere was added dropwise over 4 minutes a solution of LiHMDS (1.71 mL of a 1.0 M solution in THF, 1.71 mmol). The solution was then stirred at this temperature for 40 minutes. A solution of ethyl 3-(5-chloropyridin-3-yl)propanoate (201 mg, 0.94 mmol) in THF (1 mL) was then added dropwise via cannula over a period of 5 minutes. The reaction was stirred at −10° C. for an additional 30 minutes before being quenched with saturated aqueous ammonium chloride solution (5 mL). Volatiles were removed in vacuo, and the residue was extracted with CH$_2$Cl$_2$ (3×5 mL). The combined organic extracts were washed with water (10 mL) and brine (10 mL) before being dried, (MgSO$_4$), filtered and concentrated in vacuo. Flash chromatography (silica gel, 50% ethyl acetate in hexane) gave the title compound (228 mg, 0.52 mmol) and recovered ethyl 3-(5-chloropyridin-3-yl)propanoate (74 mg, 0.35 mmol).

$^1$H NMR (CDCl$_3$): 8.46 (m, 1 H), 8.38 (m, 1 H), 7.58 (m, 1 H), 7.21 (m, 2 H), 6.83 (m, 2 H), 3.96 (s, 2 H), 3.37 (m, 4 H), 3.17 (m, 6 H), 2.95 (dd, 2 H), MS (ESI): 442.07, 444.06, 445.1 (MH$^+$ 2×Cl).

(iii) 1-1-{[4-(4-chlorophenyl)piperazin-1-yl]sulfonyl}-4-(5-chloropyridin-3-yl)butan-2-ol

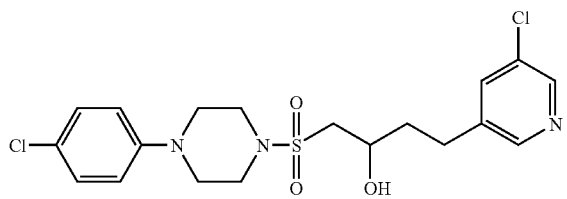

To a stirred solution of 1-{[4-(4-chlorophenyl)piperazin-1-yl]sulfonyl}-4-(5-chloropyridin-3-yl)butan-2-one (228 mg, 0.51 mmol) in a mixed solvent system of CH$_2$Cl$_2$/MeOH (1:1, 5 mL) at RT was added solid sodium borohydride in one portion. The reaction was stirred for 40 minutes before being quenched with aqueous hydrochloric acid (1 M, 2 mL). The layers were then separated and the aqueous phase extracted with CH$_2$Cl$_2$ (3×5 mL). The combined organic extracts were dried, (MgSO$_4$), filtered and concentrated in vacuo. The crude product was then filtered through a plug of silica gel, eluting with 50% ethyl acetate in hexane to give the title compound (111 mg, 0.25 mmol).

$^1$H NMR (CDCl$_3$): 8.47 (m, 1 H), 8.40 (m, 1 H), 7.59 (m, 1 H), 7.21 (m, 2H), 6.86 (m, 2 H), 4.21 (m, 1 H), 3.45 (m, 4 H), 3.24 (m, 4 H), 3.11 (m, 2H), 2.88 (m, 2 H), 1.89 (m, 2 H).

(iv) 1-(4-chlorophenyl)-4-{[(1E)-4-(5-chloropyridin-3-yl)but-1-enyl]sulfonyl}piperazine

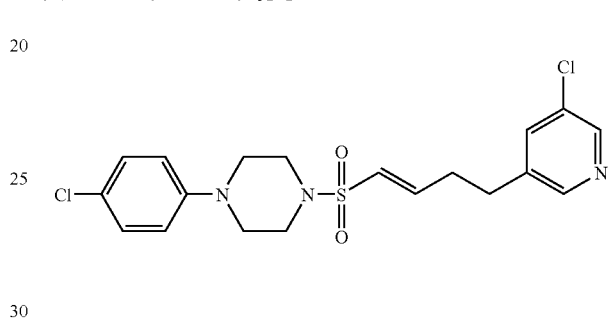

To a stirred solution of 1-{[4-(4-chlorophenyl)piperazin-1-yl]sulfonyl}-4-(5-chloropyridin-3-yl)butan-2-ol (111 mg, 0.25 mmol) in dry CH$_2$Cl$_2$ (2.5 mL) at RT was added under an atmosphere of argon, trimethylamine hydrochloride (2 mg, 0.02 mmol), triethylamine (52 μl, 0.25 mmol), then methanesulfonyl chloride (21 μl, 0.25 mmol). The reaction was stirred for 30 mins at RT, then quenched by addition of saturated aqueous sodium bicarbonate solution (5 mL). The layers were separated and the aqueous phase extracted with ethyl acetate (3×6 mL). The combined organic extracts were then dried, (MgSO$_4$), filtered and concentrated in vacuo. The residue was then dissolved in CH$_2$Cl$_2$ (2.5 mL) and treated with triethylamine (100 μl, 1.36 mmol). After 30 minutes, the reaction was quenched by addition of saturated aqueous sodium bicarbonate solution (5 mL). The layers were separated and the aqueous phase extracted with ethyl acetate (3×6 mL). The combined organic extracts were then dried, (MgSO$_4$), filtered and concentrated in vacuo. The crude material was used in the next step.

MS (ES): 446.06, 428.06, 430.07 (MH$^+$ 2×Cl)

(v) 1-(4-chlorophenyl)-4-{[4-(5-chloropyridin-3-yl)-2-(hydroxyamino)butyl]sulfonyl}piperazine

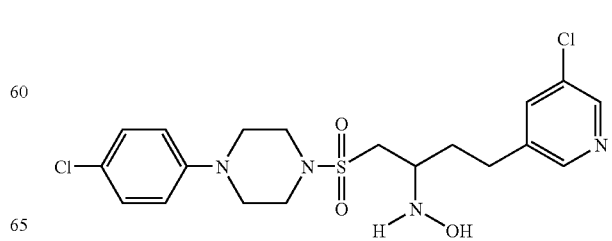

To a stirred solution of 1-(4-chlorophenyl)-4-{[(1E)-4-(5-chloropyridin-3-yl)but-1-enyl]sulfonyl}piperazine (crude from previous step), in THF (10 mL) at RT was added a solution of hydroxylamine (2 mL, 50% aqueous solution in water). The reaction was stirred for 3 hours at RT before being quenched with saturated aqueous ammonium chloride solution (5 mL). The layers were separated and the aqueous phase extracted with ethyl acetate (3×10 mL). The combined organic extracts were then dried, (MgSO$_4$), filtered and concentrated in vacuo. The residue was then purified by flash chromatography (silica, 100% ethyl acetate) to give the title compound (100 mg, 0.22 mmol).

What we claim is:

1. A compound of the formula I, or a pharmaceutically acceptable salt, or an in vivo hydrolysable ester thereof,

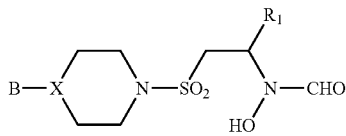

wherein
B is a 2-pyridyl or 2-pyridyloxy group monosubstituted at the 4-, 5-, or 6-position by trifluoromethyl;
X is a carbon atom;
R$_1$ is a trimethyl-1-hydantoin C$_{2-4}$alkyl or a trimethyl-3-hydantoin C$_{2-4}$alkyl group; or R$_1$ is phenyl or C$_{2-4}$alkylphenyl monosubstituted at the 3- or 4-position by halogen, trifluoromethyl, C$_{1-3}$alkyl, or C$_{1-3}$alkoxy; or R$_1$ is phenyl-SO$_2$NHC$_{2-4}$alkyl; or R$_1$ is 2-pyridyl or 2-pyridyl C$_{2-4}$alkyl; or R$_1$ is 3-pyridyl or 3-pyridyl C$_{2-4}$alkyl; or R$_1$ is 2-pyrimidine-SCH$_2$CH$_2$; or R$_1$ is 2- or 4-pyrimidinyl C$_{2-4}$alkyl optionally monosubstituted by one of halogen, trifluoromethyl, C$_{1-3}$alkyl, C$_{1-3}$alkyloxy, 2-pyrazinyl optionally substituted by halogen, or 2-pyrazinylC$_{2-4}$alkyl optionally substituted by halogen.

2. A compound as claimed in claim 1, or a pharmaceutically acceptable salt, or an in vivo hydrolysable ester thereof, wherein:
B is a 2-pyridyl or 2-pyridyloxy group monosubstituted at the 5- or 6-position by trifluoromethyl;
X is a carbon atom;
R$_1$ is a trimethyl-1-hydantoin C$_{2-4}$alkyl or a trimethyl-3-hydantoin C$_{2-4}$alkyl group; or R$_1$ is phenyl or C$_{2-4}$alkylphenyl monosubstituted at the 3- or 4-position by halogen, trifluoromethyl, C$_{1-3}$alkyl, or C$_{1-3}$alkoxy; or R$_1$ is phenyl-SO$_2$NHC$_{2-4}$alkyl; or R$_1$ is 2-pyridyl or 2-pyridylC$_{2-4}$alkyl; or R$_1$ is 3-pyridyl or 3-pyridyl C$_{2-4}$alkyl; or R$_1$ is 2-pyrimidine-SCH$_2$CH$_2$; or R$_1$ is 2- or 4-pyrimidinyl C$_{2-4}$alkyl optionally monosubstituted by one of halogen, trifluoromethyl, C$_{1-3}$alkyl, C$_{1-3}$alkyloxy, or 2-pyrazinyl or 2-pyrazinyl C$_{2-4}$alkyl.

3. A compound as claimed in claim 1, or a pharmaceutically acceptable salt, or an in vivo hydrolysable ester thereof, wherein B is selected from 4-chlorophenyl, 4-fluorophenyl, 4-bromophenyl, 4-trifluorophenyl, 5-chloro-2-pyridyl, 5-bromo-2-pyridyl, 5-fluoro-2-pyridyl, 5-trifluoromethyl-2-pyridyl, 5-cyano-2-pyridyl, and 5-methyl-2-pyridyl.

4. A compound as claimed in claim 3, or a pharmaceutically acceptable salt, or an in vivo hydrolysable ester thereof, wherein B is 4-fluorophenyl, 5-chloro-2-pyridyl, or 5-trifluoromethyl-2-pyridyl.

5. A compound as claimed in any one of the previous claims, or a pharmaceutically acceptable salt, or an in vivo hydrolysable ester thereof, wherein R$_1$ is selected from 3-chlorophenyl, 4-chlorophenyl, 3-pyridyl, 2-pyridylpropyl, 2- or 4-pyrimidinylethyl (optionally monosubstituted by fluorine), 2- or 4-pyrimidinylpropyl, and 2-(2-pyrimidinyl) propyl (optionally monosubstitued by fluorine).

6. A compound as claimed in claim 5, or a pharmaceutically acceptable salt, or an in vivo hydrolysable ester thereof wherein R$_1$ is 2-pyrimidinylpropyl, 2-(2-pyrimidinyl)propyl (optionally monosubstitued by fluorine), or 5-fluoro-2-pyrimidinylethyl.

7. A compound as claimed in claim 1, or a pharmaceutically acceptable salt, or an in vivo hydrolysable ester thereof, wherein the compound is N-[(1R or 1S)-({[4-chlorophenylpiperidino]sulfonyl}methyl)-3-[(3R or 3S)-(5-fluoropyrimidin-2-yl)butyl]N-hydroxyformamide.

8. A compound as claimed in claim 1, or a pharmaceutically acceptable salt, or an in vivo hydrolysable ester thereof, wherein the compound of formula I is the most active enantiomer.

9. A compound as claimed in claim 1, or a pharmaceutically acceptable salt, or an in vivo hydrolysable ester thereof, wherein the compound of formula I is the S enantiomer or the S,S enantiomer.

10. A pharmaceutical composition which comprises a compound as claimed in claim 1, or a pharmaceutically acceptable salt, or an in vivo hydrolysable ester thereof, and a pharmaceutically acceptable carrier.

11. A method of preparing a medicament comprising as claimed in claim 1, or a pharmaceutically acceptable salt, or in vivo hydrolysable precursor thereof, comprising combining the compound with a pharmaceutically acceptable diluent or carrier.

12. A method of treating arthritis, comprising administering a therapeutically effective amount of a compound as claimed in claim 1, or a pharmaceutically acceptable salt, or in vivo hydrolysable precursor thereof, to a subject in need of such treatment.

13. A method of treating atherosclerosis, comprising administering a therapeutically effective amount of a compound as claimed in claim 1, or a pharmaceutically acceptable salt, or in vivo hydrolysable precursor thereof, to a subject in need of such treatment.

14. A process for preparing a compound as claimed in claim 1, or a pharmaceutically acceptable salt, or in vivo hydrolysable ester thereof, which process comprises reacting a compound of the formula II with a compound of the formula R$_1$CHO to yield an alkene of the formula III, converting the alkene to a compound of the formula IV, and then converting the compound of formula IV to a compound of the formula I, and optionally thereafter forming a pharmaceutically acceptable salt or in vivo hydrolysable ester of the compound of formula I, all as set out below:

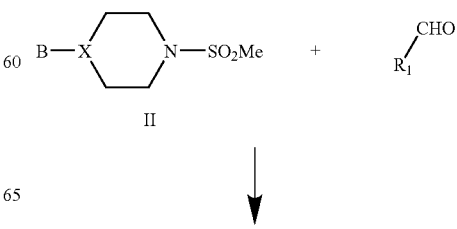

-continued

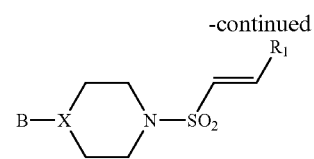

III

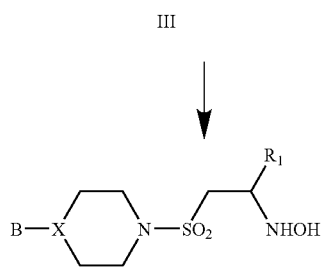

IV

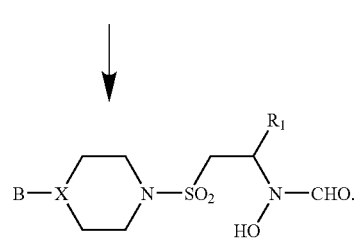

I

15. A process for preparing a compound as claimed in claim 1, or a pharmaceutically acceptable salt, or in vivo hydrolysable ester thereof, which process comprises reacting a compound of the formula II with a compound of the formula $R_1COOR$ to yield a compound of the formula VIII, converting the compound of formula VIII to a compound of the formula IX, converting the compound of formula IX to an alkene of the formula III, converting the alkene to a compound of the formula IV, and then converting the compound of formula IV to a compound of the formula I; and optionally thereafter forming a pharmaceutically acceptable salt or in vivo hydrolysable ester of the compound of formula I, all as set out below:

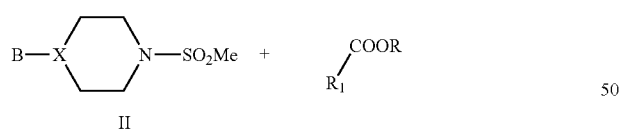

II

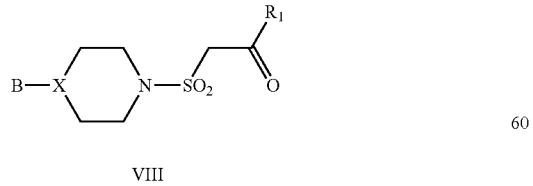

VIII

-continued

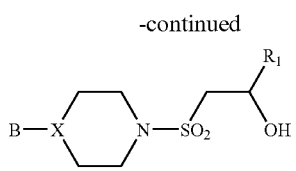

IX

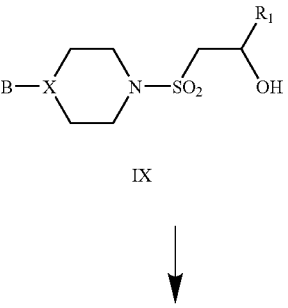

III

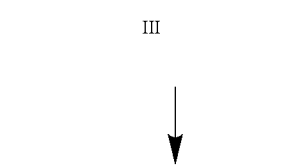

IV

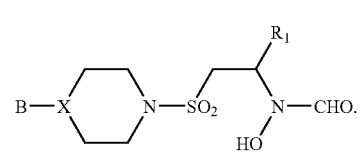

I

* * * * *